(12) United States Patent
Chen et al.

(10) Patent No.: US 9,790,563 B2
(45) Date of Patent: Oct. 17, 2017

(54) METHOD FOR TREATING LIVER CANCER

(71) Applicant: I-SHOU UNIVERSITY, Kaohsiung (TW)

(72) Inventors: Yun-Ju Chen, Kaohsiung (TW);
Wei-Chien Huang, Kaohsiung (TW);
Jhen-Yu Chen, Kaohsiung (TW);
Pei-Hsuan Chien, Kaohsiung (TW);
Wen-Shu Chen, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 503 days.

(21) Appl. No.: 14/262,266

(22) Filed: Apr. 25, 2014

(65) Prior Publication Data

US 2015/0232956 A1    Aug. 20, 2015

(30) Foreign Application Priority Data

Feb. 19, 2014   (TW) .............................. 103105475 A

(51) Int. Cl.
*C12Q 1/68* (2006.01)
*C12Q 1/70* (2006.01)

(52) U.S. Cl.
CPC ........... *C12Q 1/706* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

PUBLICATIONS

Chan DW, Ng IO. Knock-down of hepatitis B virus X protein reduces the tumorigenicity of hepatocellular carcinoma cells. J Pathol. Feb. 2006; 208(3):372-80.*
Cheng AS, Wong N, Tse AM, Chan KY, Chan KK, Sung JJ, Chan HL. RNA interference targeting HBx suppresses tumor growth and enhances cisplatin chemosensitivity in human hepatocellular carcinoma. Cancer Lett. Aug. 8, 2007; 253(1):43-52. Epub Feb. 12, 2007.*
Garrett JT, Olivares MG, Rinehart C, Granja-Ingram ND, Sánchez V, Chakrabarty A, Dave B, Cook RS, Pao W, McKinely E, Manning HC, Chang J, Arteaga CL. Transcriptional and posttranslational up-regulation of HER3 (ErbB3) compensates for inhibition of the HER2 tyrosine kinase. Proc Natl Acad Sci U S A. Mar. 22, 2011; 108(12):5021-6. Epub Mar. 8, 2011.*
Gjerdrum LM, Sorensen BS, Kjeldsen E, Sorensen FB, Nexo E, Hamilton-Dutoit S. Real-time quantitative PCR of microdissected paraffin-embedded breast carcinoma: an alternative method for HER-2/neu analysis. J Mol Diagn. Feb. 2004; 6(1):42-51.*
He Y, Sun HQ, He XE, Wang WL, Lei JH. Knockdown of HBx by RNAi inhibits proliferation and enhances chemotherapy-induced apoptosis in hepatocellular carcinoma cells. Med Oncol. Dec. 2010; 27(4):1227-33. Epub Dec. 1, 2009.*
Hsieh SY, He JR, Hsu CY, Chen WJ, Bera R, Lin KY, Shih TC, Yu MC, Lin YJ, Chang CJ, Weng WH, Huang SF. Neuregulin/erythroblastic leukemia viral oncogene homolog 3 autocrine loop contributes to invasion and early recurrence of human hepatoma. Hepatology. Feb. 2011; 53(2):504-16. Epub Jan. 18, 2011.*
Hsieh et al. Supporting Information (Epub Jan. 18, 2011., Hepatology. Feb. 2011; 53(2):504-16).*
Hsieh et al. Supporting Table 1 (Epub Jan. 18, 2011., Hepatology. Feb. 2011; 53(2):504-16).*
Jiang N, Saba NF, Chen ZG. Advances in Targeting HER3 as an Anticancer Therapy. Chemother Res Pract. 2012; 2012: 817304. pp. 1-9.*
Junttila TT, Laato M, Vahlberg T, Söderström KO, Visakorpi T, Isola J, Elenius K. Identification of patients with transitional cell carcinoma of the bladder overexpressing ErbB2, ErbB3, or specific ErbB4 isoforms: real-time reverse transcription-PCR analysis in estimation of ErbB receptor status from cancer patients. Clin Cancer Res. Nov. 1, 2003; 9(.*
Ng SA, Lee C. Hepatitis B virus X gene and hepatocarcinogenesis. J Gastroenterol. Aug. 2011; 46(8):974-90. Epub Jun. 8, 2011.*
Ledel F, Hallström M, Ragnhammar P, Öhrling K, Edler D. HER3 expression in patients with primary colorectal cancer and corresponding lymph node metastases related to clinical outcome. Eur J Cancer. Feb. 2014; 50(3):656-62. Epub Nov. 30, 2013.*
Su Q, Schröder CH, Hofmann WJ, Otto G, Pichlmayr R, Bannasch P. Expression of hepatitis B virus X protein in HBV-infected human livers and hepatocellular carcinomas. Hepatology. Apr. 1998; 27(4):1109-20.*
Wilson TR, Lee DY, Berry L, Shames DS, Settleman J. Neuregulin-1-mediated autocrine signaling underlies sensitivity to HER2 kinase inhibitors in a subset of human cancers. Cancer Cell. Aug. 16, 2011; 20(2):158-72.*
Yen CJ, Lin YJ, Yen CS, Tsai HW, Tsai TF, Chang KY, Huang WC, Lin PW, Chiang CW, Chang TT. Hepatitis B virus X protein upregulates mTOR signaling through IKKβ to increase cell proliferation and VEGF production in hepatocellular carcinoma. PLoS One. 2012; 7(7):e41931. Epub Jul. 27, 2012.*
Shin et al., "Molecular targeted therapy for hepatocellular carcinoma: Current and future", World Journal of Gastroenterology, 2013, pp. 6144-6155, vol. 19, Baishideng Publishing Group Inc., South Korea.

(Continued)

*Primary Examiner* — Samuel Woolwine
*Assistant Examiner* — Olayinka Oyeyemi
(74) *Attorney, Agent, or Firm* — Muncy, Geissler, Olds & Lowe, P.C.

(57) ABSTRACT

The invention discloses a method for evaluating therapeutic effects of lapatinib on liver cancer comprising: obtaining a liver cancer biopsy from a patient; determining level of a biomarker in the liver cancer biopsy obtained from the patient ex vivo; comparing the determined level of the biomarker in the liver cancer biopsy obtained from the patient to a reference level of the biomarker; and predicting therapeutic effect of lapatinib on liver cancer according to the comparison between the determined level and the reference level of the biomarker; wherein the reference level of the biomarker is level of the biomarker in a liver biopsy obtained from a normal, non-cancerous subject; wherein the biomarker is HBx or ErbB3.

2 Claims, 16 Drawing Sheets

(56) References Cited

PUBLICATIONS

Juliachs et al., "ErbBs inhibition by lapatinib blocks tumor growth in an orthotopic model of human testicular germ cell tumor", International Journal of Cancer, 2013, pp. 235-247, vol. 133, John Wiley & Sons, Germany.

Tanaka et al., "Molecularly targeted therapy for hepatocellular carcinoma", Liver, 2008, pp. 133-144, vol. 49, Hepato-Biliary-Pancreatic Surgery, Tokyo Medical and Dental University, Japan.

Tang, Hong, et al., The Transcriptional Transactivation Function of HBx Protein Is Important for Its Augmentation Role in Hepatitis B Virus Replication, *Journal of Virology*, May 2005, vol. 79, No. 9, pp. 5548-5556.

Liu, Jie et al., Increased expression of ErbB-2 in liver is associated with hepatitis B X antigen and shorter survival in patients with liver cancer, *Int. J. Cancer*: 125, 2009, pp. 1894-1901.

A Multi-Institutional Phase II Study of the Efficacy and Tolerability of Lapatinib in Patients with Advanced Hepatocellular Carcinomas, *Clin Cancer Res* 2009;15, Sep. 8, 2009, pp. 5895-5901.

\* cited by examiner

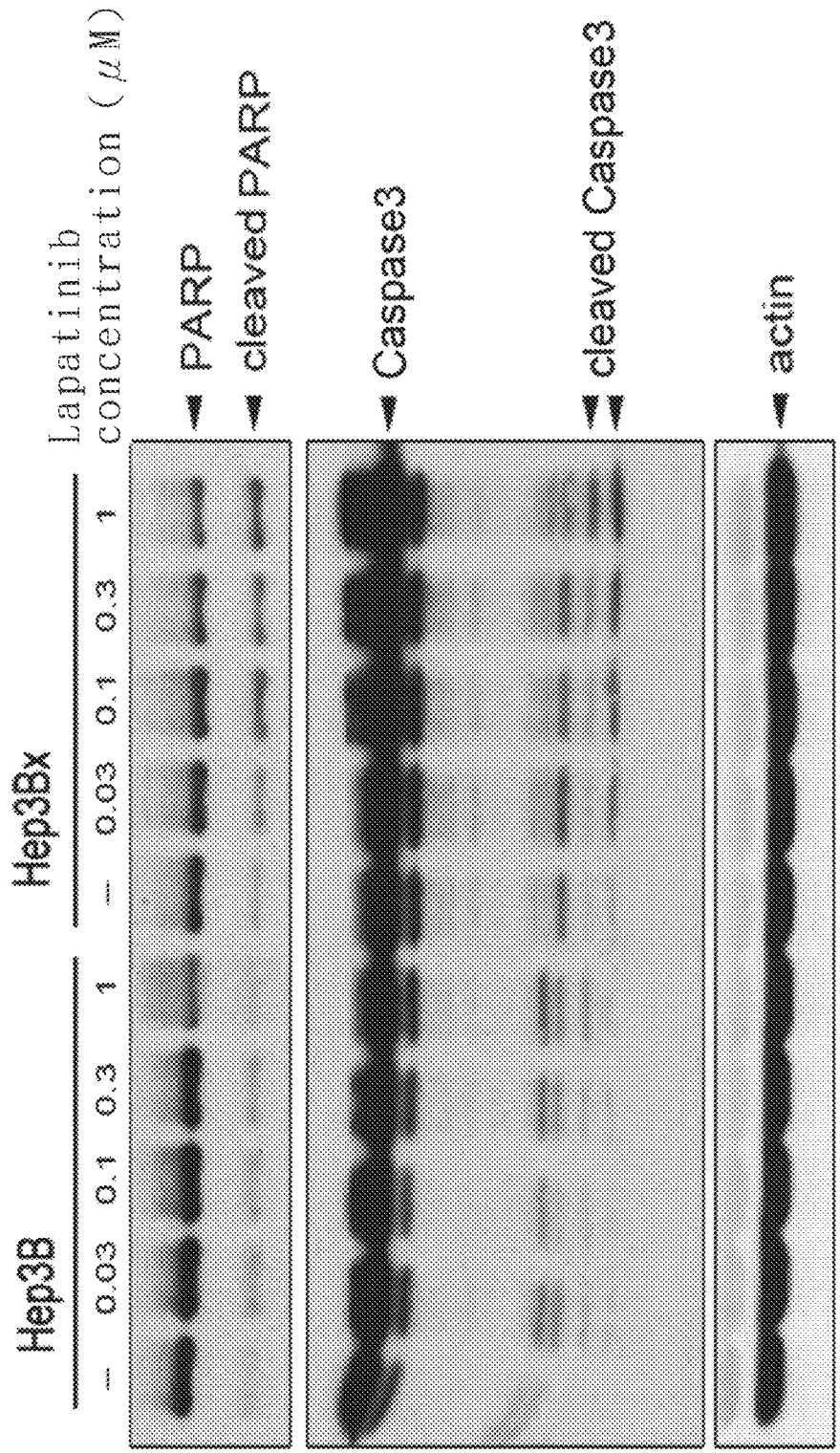

SEQUENCE LISTING

```
<160> NUMBER OF SEQ ID NOS: 13

<210> SEQ ID NO 1
<211> LENGTH: 462
<212> TYPE: DNA
<213> ORGANISM: Homo sapiens

<400> SEQUENCE: 1
atggctgcta ggctgtgctg ccaactggat ccttcgcggg acgtcctttg tttacgtccc      60
gtcggcgctg aatcccgcgg acgaccctc tcggggccgc ttgggactct ctcgtccct      120 tctccgtctg ccgttccagc cgaccacggg gcgcacctct ctttacgcgg tctccccgtc     180
tgtgccttct catctgccgg accgtgtgca cttcgcttca cctctgcacg tagcatggag     240 accacgtga acgcccacca ggtcttgccc aaggtcttac acaagaggac tcttggactc     300
```

| | |
|---|---|
| tcagcaatgt caacgaccga ccttgaggca tacttcaaag actgtttgtt taaagactgg | 360 |
| gaggagttgg gggaggagat taggttaaag gtctttgtat taggaggctg tgggcataaa | 420 |
| ttggtctgcg caccagcacc atgcaacttt ttcacctctg cc | 462 |

<210> SEQ ID NO 2
<211> LENGTH: 154
<212> TYPE: PRT
<213> ORGANISM: Homo sapiens

<400> SEQUENCE: 2

```
Met Ala Ala Arg Leu Cys Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly Thr Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Ser Met Glu
65                  70                  75                  80

Thr Thr Val Asn Ala His Gln Val Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Gly His Lys Leu Val Cys Ala
    130                 135                 140

Pro Ala Pro Cys Asn Phe Phe Thr Ser Ala
145                 150
```

<210> SEQ ID NO 3
<211> LENGTH: 4026
<212> TYPE: DNA
<213> ORGANISM: Homo sapiens

<400> SEQUENCE: 3

| | |
|---|---|
| atgagggcga acgacgctct gcaggtgctg ggcttgcttt tcagcctggc ccggggctcc | 60 |
| gaggtgggca actctcaggc agtgtgtcct gggactctga atggcctgag tgtgaccggc | 120 |
| gatgctgaga accaatacca gacactgtac aagctctacg agaggtgtga ggtggtgatg | 180 |
| gggaaccttg agattgtgct cacgggacac aatgccgacc tctccttcct gcagtggatt | 240 |
| cgagaagtga caggctatgt cctcgtggcc atgaatgaat tctctactct accattgccc | 300 |
| aacctccgcg tggtgcgagg gacccaggtc tacgatggga agtttgccat cttcgtcatg | 360 |
| ttgaactata acaccaactc cagccacgct ctgcgccagc tccgcttgac tcagctcacc | 420 |
| gagattctgt caggggtgt ttatattgag aagaacgata agctttgtca catggacaca | 480 |
| attgactgga gggacatcgt gagggaccga gatgctgaga tagtggtgaa ggacaatggc | 540 |
| agaagctgtc cccctgtca tgaggtttgc aaggggcgat gctggggtcc tggatcagaa | 600 |
| gactgccaga cattgaccaa gaccatctgt gctcctcagt gtaatggtca ctgctttggg | 660 |
| cccaacccca accagtgctg ccatgatgag tgtgccgggg gctgctcagg ccctcaggac | 720 |
| acagactgct tgcctgccg gcacttcaat gacagtggag cctgtgtacc tcgctgtcca | 780 |
| cagcctcttg tctacaacaa gctaactttc cagctggaac ccaatcccca caccaagtat | 840 |

```
cagtatggag gagtttgtgt agccagctgt ccccataact ttgtggtgga tcaaacatcc    900
tgtgtcaggg cctgtcctcc tgacaagatg gaagtagata aaaatgggct caagatgtgt    960
gagccttgtg ggggactatg tcccaaagcc tgtgagggaa caggctctgg gagccgcttc   1020
cagactgtgg actcgagcaa cattgatgga tttgtgaact gcaccaagat cctgggcaac   1080
ctggactttc tgatcaccgg cctcaatgga gacccctggc acaagatccc tgccctggac   1140
ccagagaagc tcaatgtctt ccggacagta cgggagatca caggttacct gaacatccag   1200
tcctggccgc cccacatgca caacttcagt gttttttcca atttgacaac cattggaggc   1260
agaagcctct acaaccgggg cttctcattg ttgatcatga agaacttgaa tgtcacatct   1320
ctgggcttcc gatccctgaa ggaaattagt gctgggcgta tctatataag tgccaatagg   1380
cagctctgct accaccactc tttgaactgg accaaggtgc ttcgggggcc tacgaagag    1440
cgactagaca tcaagcataa tcggccgcgc agagactgcg tggcagaggg caaagtgtgt   1500
gacccactgt gctcctctgg gggatgctgg ggcccaggcc ctggtcagtg cttgtcctgt   1560
cgaaattata gccgaggagg tgtctgtgtg acccactgca actttctgaa tggggagcct   1620
cgagaatttg cccatgaggc cgaatgcttc tcctgccacc cggaatgcca acccatggag   1680
ggcactgcca catgcaatgg ctcgggctct gatacttgtg ctcaatgtgc ccattttcga   1740
gatgggcccc actgtgtgag cagctgcccc catggagtcc taggtgccaa gggcccaatc   1800
tacaagtacc cagatgttca gaatgaatgt cggccctgcc atgagaactg cacccagggg   1860
tgtaaaggac cagagcttca agactgttta ggacaaacac tggtgctgat cggcaaaacc   1920
catctgacaa tggcttttgac agtgatagca ggattggtag tgatttttcat gatgctgggc   1980
ggcactttc tctactggcg tgggcgccgg attcagaata aagggctat gaggcgatac     2040
ttggaacggg gtgagagcat agagcctctg gaccccagtg agaaggctaa caaagtcttg    2100
gccagaatct tcaaagagac agagctaagg aagcttaaag tgcttggctc gggtgtcttt    2160
ggaactgtgc acaaaggagt gtggatccct gagggtgaat caatcaagat tccagtctgc    2220
attaaagtca ttgaggacaa gagtggacgg cagagttttc aagctgtgac agatcatatg    2280
ctggccattg gcagcctgga ccatgcccac attgtaaggc tgctgggact atgcccaggg    2340
tcatctctgc agcttgtcac tcaatatttg cctctgggtt ctctgctgga tcatgtgaga    2400
caacaccggg gggcactggg gccacagctg ctgctcaact ggggagtaca aattgccaag    2460
ggaatgtact accttgagga acatggtatg gtgcatagaa acctggctgc ccgaaacgtg    2520
ctactcaagt cacccagtca ggttcaggtg gcagattttg tgtggctga cctgctgcct    2580
cctgatgata gcagctgct atacagtgag gccaagactc caattaagtg atggcccctt    2640
gagagtatcc actttgggaa atacacacac cagagtgatg tctggagcta tggtgtgaca    2700
gtttgggagt tgatgacctt cggggcagag ccctatgcag ggctacgatt ggctgaagta    2760
ccagacctgc tagagaaggg ggagcggttg gcacagcccc agatctgcac aattgatgtc    2820
tacatggtga tggtcaagtg ttggatgatt gatgagaaca ttcgcccaac ctttaaagaa    2880
ctagccaatg agttcaccag gatggcccga gacccaccac ggtatctggt cataaagaga    2940
gagagtgggc ctggaatagc ccctgggcca gagccccatg gtctgacaaa caagaagcta    3000
gaggaagtag agctggagcc agaactagac ctagacctag acttggaagc agaggaggac    3060
aacctggcaa ccaccacact gggctccgcc tcagcctac cagttggaac acttaatcgg     3120
ccacgtggga gccagagcct tttaagtcca tcatctggat acatgcccat gaaccaggt    3180
```

-continued

```
aatcttgggg agtcttgcca ggagtctgca gtttctggga gcagtgaacg gtgcccccgt    3240
ccagtctctc tacacccaat gccacgggga tgcctggcat cagagtcatc agagggcat     3300 gtaacaggct ctgaggctga gctccaggag aaagtgtcaa tgtgtaggag ccggagcagg    3360
agccggagcc cacggccacg cggagatagc gcctaccatt cccagcgcca cagtctgctg    3420
actcctgtta ccccactctc cccacccggg ttagaggaag aggatgtcaa cggttatgtc    3480
atgccagata cacacctcaa aggtactccc tcctcccggg aaggcaccct ttcttcagtg    3540
ggtctcagtt ctgtcctggg tactgaagaa gaagatgaag atgaggagta tgaatacatg    3600
aaccggagga gaaggcacag tccacctcat cccctaggc caagttccct tgaggagctg     3660
ggttatgagt acatggatgt ggggtcagac ctcagtgcct ctctgggcag cacacagagt    3720 tgccactcc accctgtacc catcatgccc actgcaggca caactccaga tgaagactat      3780
gaatatatga atcggcaacg agatggaggt ggtcctgggg gtgattatgc agccatgggg    3840
gcctgcccag catctgagca agggtatgaa gagatgagag cttttcaggg gcctggacat    3900
caggcccccc atgtccatta tgcccgccta aaaactctac gtagcttaga ggctacagac    3960
tctgcctttg ataaccctga ttactggcat agcaggcttt ccccaaggc taatgcccag      4020 agaacg                                                               4026
```

<210> SEQ ID NO 4
<211> LENGTH: 1342
<212> TYPE: PRT
<213> ORGANISM: Homo sapiens

<400> SEQUENCE: 4

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220
```

```
Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
        260                 265                 270

Glu Pro Asn Pro His Thr Lys Tyr Gln Tyr Gly Gly Val Cys Val Ala
    275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
        340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
        420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
        500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
        580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640
```

-continued

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
            930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Glu Ser Cys Gln Glu

```
                    1055                1060                1065
Ser Ala Val Ser Gly Ser Ser Glu Arg Cys Pro Arg Pro Val Ser
            1070                1075                1080
Leu His Pro Met Pro Arg Gly Cys Leu Ala Ser Glu Ser Ser Glu
            1085                1090                1095
Gly His Val Thr Gly Ser Glu Ala Glu Leu Gln Glu Lys Val Ser
            1100                1105                1110
Met Cys Arg Ser Arg Ser Arg Ser Arg Ser Pro Arg Pro Arg Gly
            1115                1120                1125
Asp Ser Ala Tyr His Ser Gln Arg His Ser Leu Leu Thr Pro Val
            1130                1135                1140
Thr Pro Leu Ser Pro Pro Gly Leu Glu Glu Glu Asp Val Asn Gly
            1145                1150                1155
Tyr Val Met Pro Asp Thr His Leu Lys Gly Thr Pro Ser Ser Arg
            1160                1165                1170
Glu Gly Thr Leu Ser Ser Val Gly Leu Ser Ser Val Leu Gly Thr
            1175                1180                1185
Glu Glu Glu Asp Glu Asp Glu Glu Tyr Glu Tyr Met Asn Arg Arg
            1190                1195                1200
Arg Arg His Ser Pro Pro His Pro Pro Arg Pro Ser Ser Leu Glu
            1205                1210                1215
Glu Leu Gly Tyr Glu Tyr Met Asp Val Gly Ser Asp Leu Ser Ala
            1220                1225                1230
Ser Leu Gly Ser Thr Gln Ser Cys Pro Leu His Pro Val Pro Ile
            1235                1240                1245
Met Pro Thr Ala Gly Thr Thr Pro Asp Glu Asp Tyr Glu Tyr Met
            1250                1255                1260
Asn Arg Gln Arg Asp Gly Gly Gly Pro Gly Gly Asp Tyr Ala Ala
            1265                1270                1275
Met Gly Ala Cys Pro Ala Ser Glu Gln Gly Tyr Glu Glu Met Arg
            1280                1285                1290
Ala Phe Gln Gly Pro Gly His Gln Ala Pro His Val His Tyr Ala
            1295                1300                1305
Arg Leu Lys Thr Leu Arg Ser Leu Glu Ala Thr Asp Ser Ala Phe
            1310                1315                1320
Asp Asn Pro Asp Tyr Trp His Ser Arg Leu Phe Pro Lys Ala Asn
            1325                1330                1335
Ala Gln Arg Thr
            1340

<210> SEQ ID NO 5
<211> LENGTH: 30
<212> TYPE: DNA
<213> ORGANISM: Artificial Sequence
<220> FEATURE:
<223> OTHER INFORMATION: Primer for Constructing myc-HBx

<400> SEQUENCE: 5
gttaagctta tggctgctag gctgtgctgc                                    30

<210> SEQ ID NO 6
<211> LENGTH: 32
<212> TYPE: DNA
<213> ORGANISM: Artificial Sequence
<220> FEATURE:
<223> OTHER INFORMATION: Primer for Constructing myc-HBx
```

<400> SEQUENCE: 6
agactcgagc cgggcagagg tgaaaaagtt gc                          32

<210> SEQ ID NO 7
<211> LENGTH: 57
<212> TYPE: DNA
<213> ORGANISM: Artificial Sequence
<220> FEATURE:
<223> OTHER INFORMATION: Primer for Constructing pDEST-V5-HBx

<400> SEQUENCE: 7
ggggacaagt ttgtacaaaa aagcaggctt aatggctgct aggctgtgct gccaatg    57

<210> SEQ ID NO 8
<211> LENGTH: 48
<212> TYPE: DNA
<213> ORGANISM: Artificial Sequence
<220> FEATURE:
<223> OTHER INFORMATION: Primer for Constructing pDEST-V5-HBx

<400> SEQUENCE: 8
ggggaccact ttgtacaaga aagctgggtc atggtgatgg tgatgatg         48

<210> SEQ ID NO 9
<211> LENGTH: 19
<212> TYPE: DNA
<213> ORGANISM: Artificial Sequence
<220> FEATURE:
<223> OTHER INFORMATION: siRNA for Silencing HBx Gene Expression

<400> SEQUENCE: 9
ggttaaaggt ctttgtatt                                         19

<210> SEQ ID NO 10
<211> LENGTH: 19
<212> TYPE: DNA
<213> ORGANISM: Artificial Sequence
<220> FEATURE:
<223> OTHER INFORMATION: Control siRNA

<400> SEQUENCE: 10
gatcatacgt gcgatcaga                                         19

<210> SEQ ID NO 11
<211> LENGTH: 26
<212> TYPE: DNA
<213> ORGANISM: Artificial Sequence
<220> FEATURE:
<223> OTHER INFORMATION: Primer for Constructing pDSRed-ErbB3

<400> SEQUENCE: 11
gagctcatga gggcgaacga cgctct                                 26

<210> SEQ ID NO 12
<211> LENGTH: 26
<212> TYPE: DNA
<213> ORGANISM: Artificial Sequence
<220> FEATURE:
<223> OTHER INFORMATION: Primer for Constructing pDSRed-ErbB3

<400> SEQUENCE: 12
ggtaccttac gttctctggg cattag                                 26

<210> SEQ ID NO 13
<211> LENGTH: 19

```
<212> TYPE: DNA
<213> ORGANISM: Artificial Sequence
<220> FEATURE:
<223> OTHER INFORMATION: siRNA for Silencing ErbB3 Gene Expression

<400> SEQUENCE: 13
gcgatgctga gaaccaata                                                    19
```

METHOD FOR TREATING LIVER CANCER

BACKGROUND OF THE INVENTION

1. Field of the Invention

The present invention generally relates to a method for evaluating therapeutic effects of lapatinib on liver cancer and, more particularly, to a method for evaluating therapeutic effects of lapatinib on liver cancer by using a biomarker as level of HBx or ErbB3.

2. Description of the Related Art

Liver cancers are common malignant tumors that grow on the surface or inside the liver. Generally, liver cancers are considered to associate with hepatitis B viral infection, cirrhosis, alcohol consumption and aflatoxin B1 contamination of food. It's worth noting that hepatitis B viral (HBV) infection is the primary cause of liver cancers. HBx, with one of regulatory gene encoded by genomic sequence as set forth in SEQ ID NO. 1, is a hepatitis B viral gene. After hepatitis B viral infection, HBx can be expressed as HBx, with an amino acid sequence as set forth in SEQ ID NO. 2, in patients. Moreover, HBx plays an important role in pathogenesis of HBV-associated liver cancer.

In general, in the early stage as tumor size less than 5 cm, the tumor can be removed by surgical resection with a good prognosis. However, because no obvious symptom is occurred in the early stage, most patients know they suffer from liver cancer until advanced stage with a high lethality. Liver cancers have complicated pathogenesis. Sorafenib is a clinically conventional drug for liver cancer. However, some patients have drug resistance. In light of this, it is necessary to develop a novel drug for liver cancer.

Lapatinib, a dual tyrosine kinase inhibitor interrupting the HER2/neu and EGFR pathway, is a conventional drug for breast cancer. However, whether lapatinib can be applied to treat other cancers is still unknown.

In clinical trial, scientists demonstrate that lapatinib is effective for only part of patients with liver cancers. In light of this, it is necessary to develop a method for defining the liver cancer patients on which lapatinib poses therapeutic effect.

SUMMARY OF THE INVENTION

It is therefore the objective of this invention to provide a method for evaluating therapeutic effects of lapatinib on liver cancer, by detecting level of a biomarker and further grouping liver cancer patients into patients suitable for lapatinib treatment.

One embodiment of the invention discloses a method for evaluating therapeutic effects of lapatinib on liver cancer comprising: obtaining a liver cancer biopsy from a patient; determining level of a biomarker in the liver cancer biopsy obtained from the patient ex vivo; comparing the determined level of the biomarker in the liver cancer biopsy obtained from the patient to a reference level of the biomarker; and predicting therapeutic effect of lapatinib on liver cancer according to the comparison between the determined level and the reference level of the biomarker; wherein the reference level of the biomarker is level of the biomarker in a liver cancer biopsy obtained from a normal, non-cancerous subject; wherein the biomarker is HBx or ErbB3.

In a preferred form shown, the level of the biomarker is determined by real-time PCR.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 3 shows protein level of components of apoptotic signaling pathway in the Hep3B and Hep3Bx cells after lapatinib treatment.

Figure 1A:
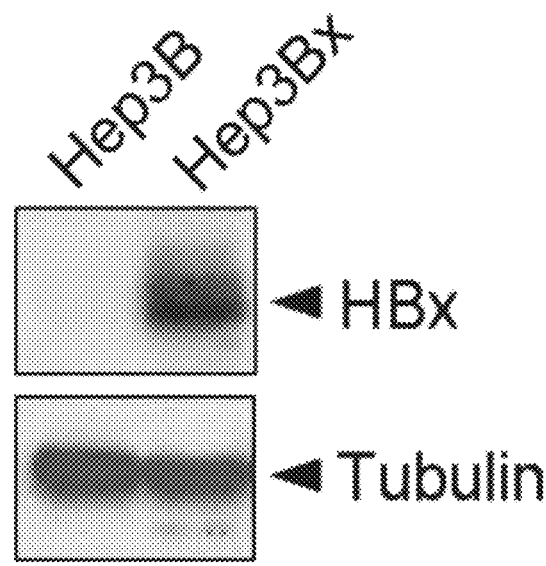
FIG. 1a shows protein level of HBx in the Hep3B and Hep3Bx cells.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method for evaluating therapeutic effects of lapatinib on liver cancer according to preferred teachings of the invention comprises: obtaining a liver cancer biopsy from a patient; determining level of a biomarker in the liver cancer biopsy obtained from the patient ex vivo; comparing the determined level of the biomarker in the liver cancer biopsy obtained from the patient to a reference level of the biomarker; and predicting therapeutic effect of lapatinib on liver cancer according to the comparison between the determined level and the reference level of the biomarker; wherein the biomarker is HBx or ErbB3.

In detail, the liver cancer biopsy is obtained from cancerous liver tissue of the patient. Preferably, the liver cancer biopsy can be obtained via pacutaneous biopsy, transjugulan biopsy or laparoscopic biopsy. Alternatively, the liver cancer biopsy can be obtained via surgery, which is a well-known process in this field.

The level of HBx or ErbB3 in the liver cancer biopsy obtained from the patient can be determined ex vivo. The level of HBx or ErbB3 indicates mRNA or protein level. For example, the protein level can be determined by performing immunohistochemistry staining with a HBx-specific or ErbB3-specific antibody. Alternatively, the protein level can be determined by extracting total protein from the liver cancer biopsy and then performed Western blotting or ELISA with the HBx-specific or ErbB3-specific antibody. Moreover, the mRNA level can be determined by extracting total RNA from the liver cancer biopsy, followed by performing Northern blotting with a HBx mRNA-specific or ErbB3 mRNA-specific probe. Also, the total RNA can be converted to cDNA by reverse transcriptase and detecting cDNA level of HBx or ErbB3 by using an expression array or by performing real-time PCR.

The determined level of HBx or ErbB3 is further compared with the reference level of HBx or ErbB3. The reference level of HBx or ErbB3 indicates the protein or mRNA level of HBx or ErbB3 in a liver biopsy obtained from a normal, non-cancerous subject. According to the comparison between the determined level and the reference level of HBx or ErbB3, the therapeutic effect of lapatinib on liver cancer can be predicted. For example, since HBx is a hepatitis B virus-specific gene and the normal, non-cancerous subject has the reference level of HBx of 0, the patient with the determined level of HBx more than 0 is suitable for lapatinib treatment. That is, lapatinib has a better therapeutic effect on liver cancer of the patient with expressing HBx mRNA or protein. Also, compared with the normal, non-cancerous subject with a lower reference level of ErbB3, the patient with a higher determined level of ErbB3 is suitable for lapatinib treatment. In other words, lapatinib has a better therapeutic effect on liver cancer of the patient with the higher expressing ErbB3 mRNA or protein.

According to the level of HBx or ErbB3 in the liver cancer biopsy, the patients can be grouped into patients suitable for lapatinib treatment and patients unsuitable for lapatinib treatment. Physicians are able to apply lapatinib as an anti-liver cancer drug to the former patients and thereby improving the therapeutic effects of lapatinib on liver cancer.

To prove HBx or ErbB3 can be used as a biomarker for evaluating the intolerance of liver cancer on lapatinib and the therapeutic effect of lapatinib on liver cancer, following trials are performed:

In the following trials, liver cancer cells including Hep3B, Hep3Bx, HepG2 and HepG2x cells are used. The Hep3Bx and HepG2x cells, derived from the Hep3B and HepG2 cells, respectively, are cell lines constitutively expressing HBx. All of the liver cancer cells are incubated in a 37° C. incubator. DME/F12 with 10% FBS is used as media for incubating the cell lines. Moreover, lapatinib is dissolved in DMSO with different concentration.

Trial (A). Lapatinib shows cytotoxicity to the Hep3Bx cells but not to the Hep3B cells.

Cell lysates are prepared by lysing $5\times10^6$ of the Hep3B and Hep3Bx cells in 0.2 mL of RIPA buffer, respectively. To confirm the expression of HBx, Western blotting is performed with anti-HBx antibody (1: 1,000, purchased from Abcam). The anti-Tubulin antibody is used as an internal control. Referring to FIG. 1a, HBx protein expresses in the Hep3Bx cells but not the Hep3B cells.

Cytotoxicity of lapatinib to the Hep3B and Hep3Bx cells is monitored using the MTT 3-(4,5-dimethylthiazol-2-yl)-2, 5-diphenyltetrazolium bromide assay. First, the Hep3B and Hep3Bx cells are inoculated in a 96-well pate with 5,000-10,000 cells per well. After incubating at 37° C. for 24 hours, 0, 0.1, 0.5, 1, 5 and 10 μM of lapatinib is added into the medium for further incubation at 37° C. for 72 hours, respectively. 0.025 mL of MTT solution (0.001 mg of MTT dissolved in 1 mL of 1×PBS) is added into 0.1 mL of the medium, followed by incubating at 37° C. for 4 hours. Succinate dehydrogenase, bound to the inner mitochondrial membrane of the living cells, is capable of reducing MTT to its insoluble formazan, which has a purple color. Therefore, after removing the supernatants, 0.1 mL of DMSO is added to dissolve the insoluble formazan into a colored solution. The absorbance of the colored solution is quantified by measuring at 570 nm by a spectrophotometer.

Figure 1B:
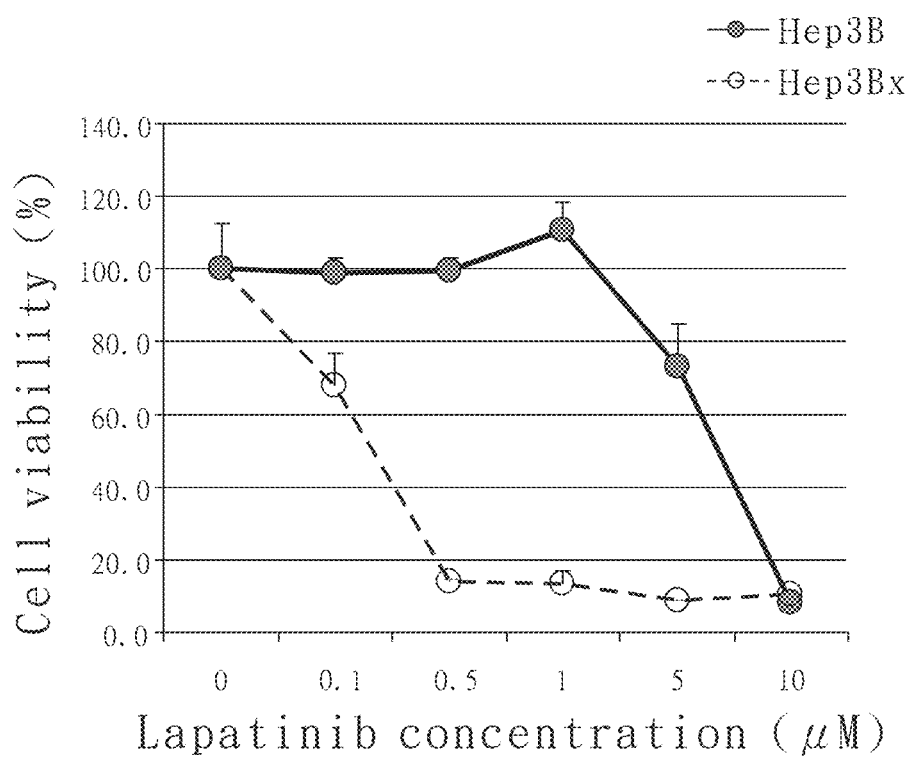
FIG. 1b shows cell viability of the Hep3B and Hep3Bx cells after lapatinib treatment.

Referring to FIG. 1b, the Hep3B cells show intolerance of lapatinib with concentration more than 5 μM. On the contrary, the Hep3Bx cells show intolerance of lapatinib with concentration more than 0.1 μM. That is, lapatinib shows cytotoxicity to the Hep3Bx cells.

Trial (B). Lapatinib induces apoptosis in the Hep3Bx cells but not in the Hep3B cells.

The Hep3B and Hep3Bx cells are inoculated in 3.5-cm petri dishes, respectively. After the Hep3B and Hep3Bx cells cover 50 to 60% of the 3.5-cm petri dishes, 3 mL of fresh medium with different concentrations of lapatinib is added, followed by incubation at 37° C. for 120 hours. The cultured Hep3B and Hep3Bx cells are resuspended in 3 mL of 75% ethanol in a concentration of $1.5\times10^5$ cells per mL and fixed at −20° C. for at least 2 hours. Finally, the fixed Hep3B and Hep3Bx cells are mixed with 0.5 mL of PI buffer at 37° C. for 30 minutes. The sub-G1 phase arresting cells with a DNA content less than 2n, which are usually the result of apoptotic DNA fragmentation are detected and measured by a sub-G1 peak in the fluorescence histogram of flow cytometry.

Figure 2:
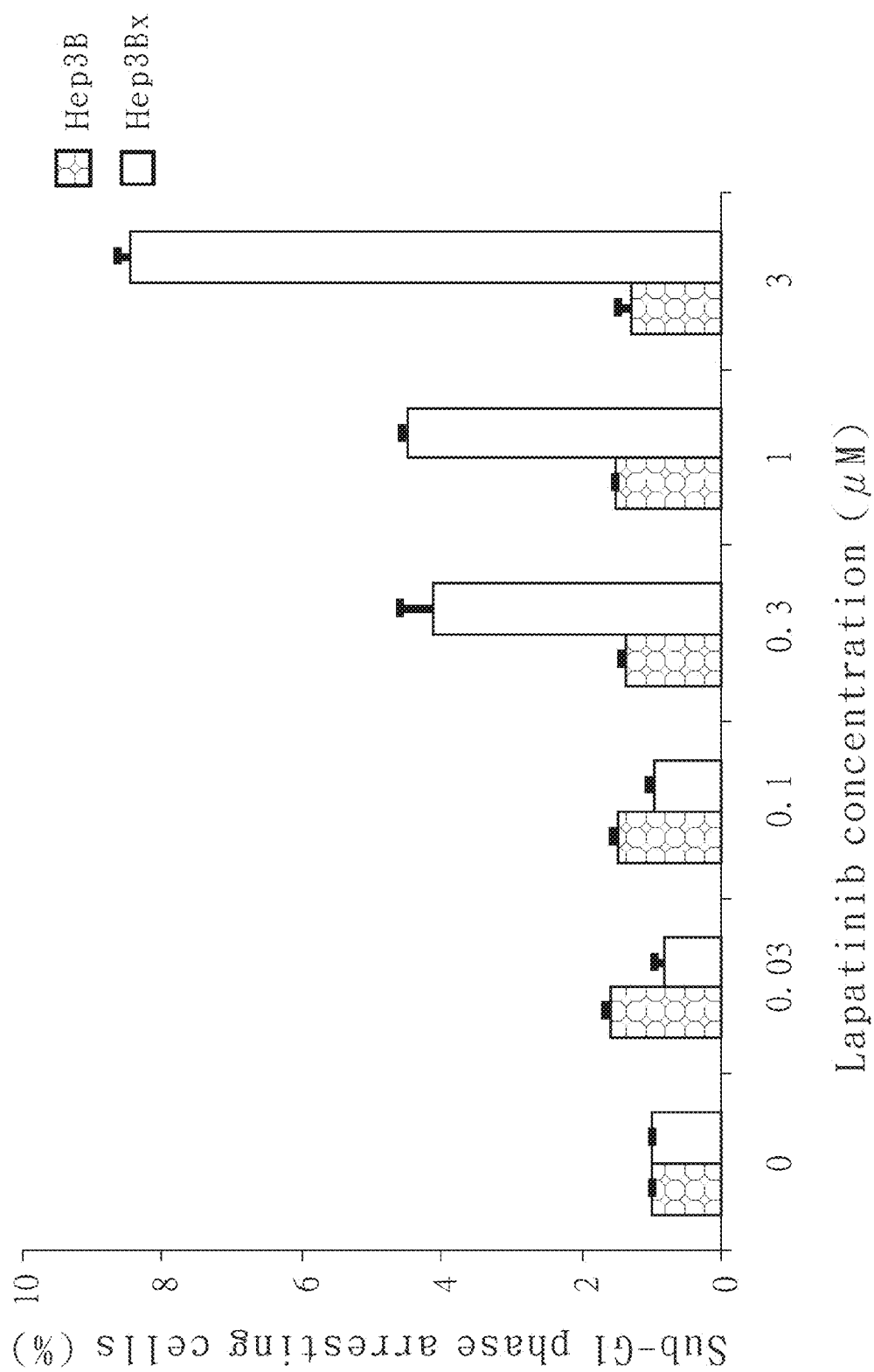
FIG. 2 shows sub-G1 phase arrest of the Hep3B and Hep3Bx cells after lapatinib treatment.

Referring to FIG. 2, lapatinib treatment does not trigger sub-G1 phase arrest in the Hep3B cells. However, the higher the treating concentration is, the more sub-G1 phase arresting cells are observed in the Hep3Bx cells. That is, lapatinib is capable of inducing the Hep3Bx cells to undergo apoptosis.

Trial (C). Lapatinib triggers apoptotic signaling pathway in the Hep3Bx cells but not in the Hep3B cells.

To further confirm the apoptotic signaling pathway in the Hep3B and Hep3Bx cells, the lapatinib-treated Hep3B and Hep3Bx cells are lysed in 0.2 mL of RIPA buffer, respectively. Western blotting is performed with anti-PARP antibody (1: 1,000, purchased from Cell Signaling) and anti-Caspase-3 antibody (1: 1,000, purchased from Cell Signaling). The anti-Actin antibody (1: 10,000, purchased from Sigma) is used as an internal control.

Referring to FIG. 3, lapatinib treatment does not increase the level of cleaved PARP and cleaved Caspase-3 in the Hep3B cells. However, the Hep3Bx cells with lapatinib treatment in a higher concentration show higher level of cleaved PARP and cleaved Caspase-3. That is, lapatinib treatment triggers the apoptotic signaling pathway in the Hep3Bx cells.

In the trial (D) and (E), HBx is introduced into the Hep3B cells via transient transfection and virus transduction, respectively. Cytotoxicity of lapatinib to the HBx-transfected or HBx-virus transduced Hep3B cells is further monitored by the crystal violet assay.

Trial (D). Lapatinib shows cytotoxicity to the myc-HBx-transfected Hep3B cells.

The plasmids used to transiently transfect into the Hep3B cells in the trial (D) are shown in TABLE 1. That is, pcDNA6/myc-His A vector is used as a control (group D1) and the C-terminal myc-tagged HBx plasmid expressing myc-HBx expression protein constructed with primers with sequences set forth in SEQ ID NOs. 5 and 6 is used as the group D2.

TABLE 1

| Groups | Plasmids |
| --- | --- |
| D1 | Vector (pcDNA6/myc-His A) |
| D2 | myc-HBx |

The plasmids are transfected into the Hep3B cells as the following procedure: 1 μg of the plasmids are mixed with 1 μL of TransIT2020 transfection reagent, and the mixture is incubated with the fresh medium without FBS at room temperature for 30 minutes to obtain the vector-transfected Hep3B cells (group D1) and the myc-HBx-transfected Hep3B cells (group D2).

Figure 4A:
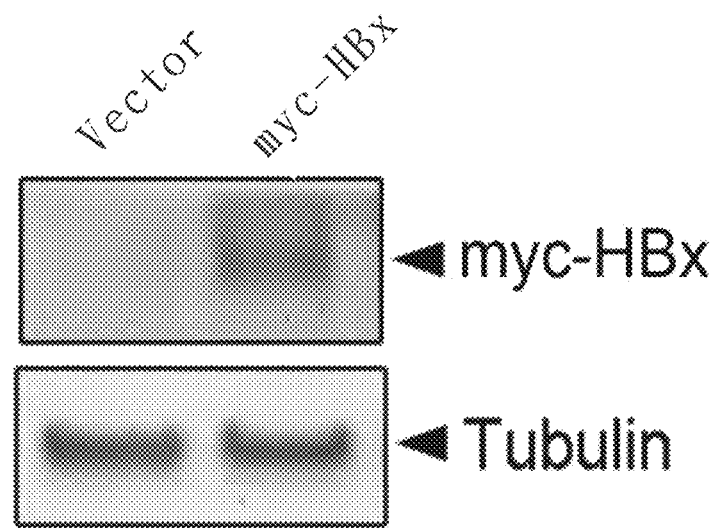
FIG. 4a shows protein level of myc-HBx in the vector- and myc-HBx-transfected Hep3B cells.

The transiently transfected Hep3B cells are lysed in 0.2 mL of RIPA buffer, respectively. To confirm the expression of myc-HBx, Western blotting is performed with anti-myc antibody (1: 5,000, purchased from Sigma). The anti-Tubulin antibody (1: 10,000, purchased from Sigma) is used as an internal control. Referring to FIG. 4a, HBx protein only expresses in the myc-HBx-transfected Hep3B cells (group D2) but not in the vector-transfected Hep3B cells (group D1).

Figure 4B:
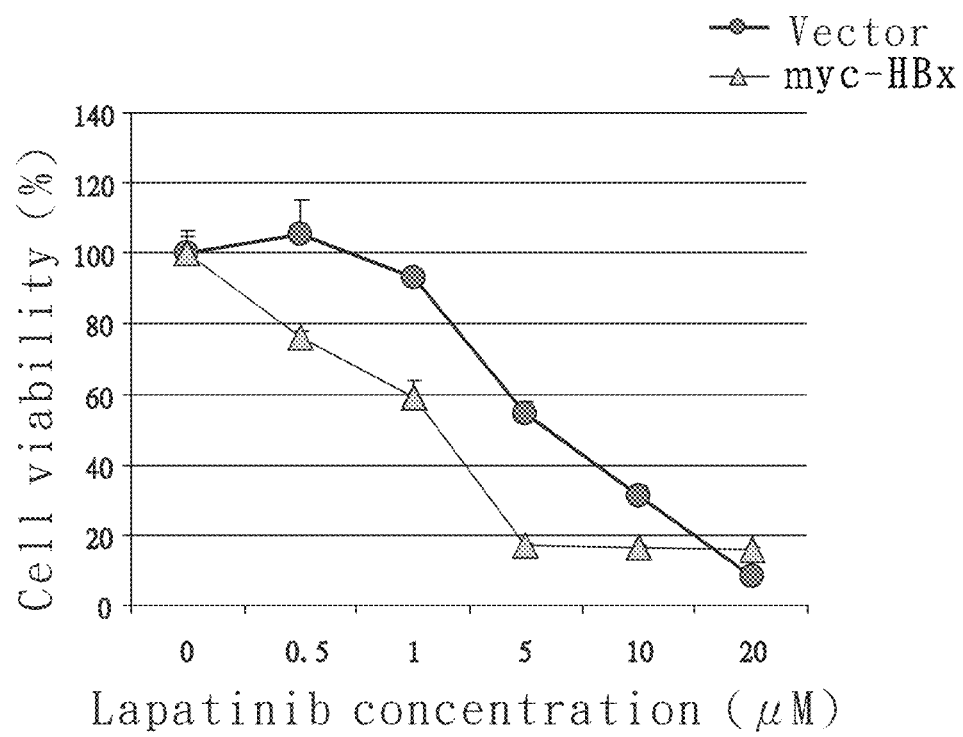
FIG. 4b shows cell viability of the vector- and myc-HBx-transfected Hep3B cells after lapatinib treatment.

Furthermore, referring to FIG. 4b, lapatinib shows cytotoxicity to the vector-transfected Hep3B cells (group D1) in a concentration of 5 μM. On the other hand, lapatinib shows cytotoxicity to the myc-HBx-transfected Hep3B cells (group D2) in a concentration of 1 μM. That is, myc-HBx introduction increases intolerance to lapatinib of the Hep3B cells.

Moreover, $1 \times 10^5$ cells of the vector-transfected Hep3B cells (group D1) and the myc-HBx-transfected Hep3B cells (group D2) are further treated with 1 μM of lapatinib. Also, DMSO is used to treat the vector-transfected Hep3B cells (group D1) and the myc-HBx-transfected Hep3B cells (group D2) as a solvent control. After culturing at 37° C. for 120 hours, the supernatants are removed and 10 mg/mL of crystal violet solution dissolving in 30% ethanol is added to the cultured Hep3B cells for 15 to 30 minutes. Crystal violet solution can stain the nuclei of the living cells adhering to the petri dishes.

Figure 4C:
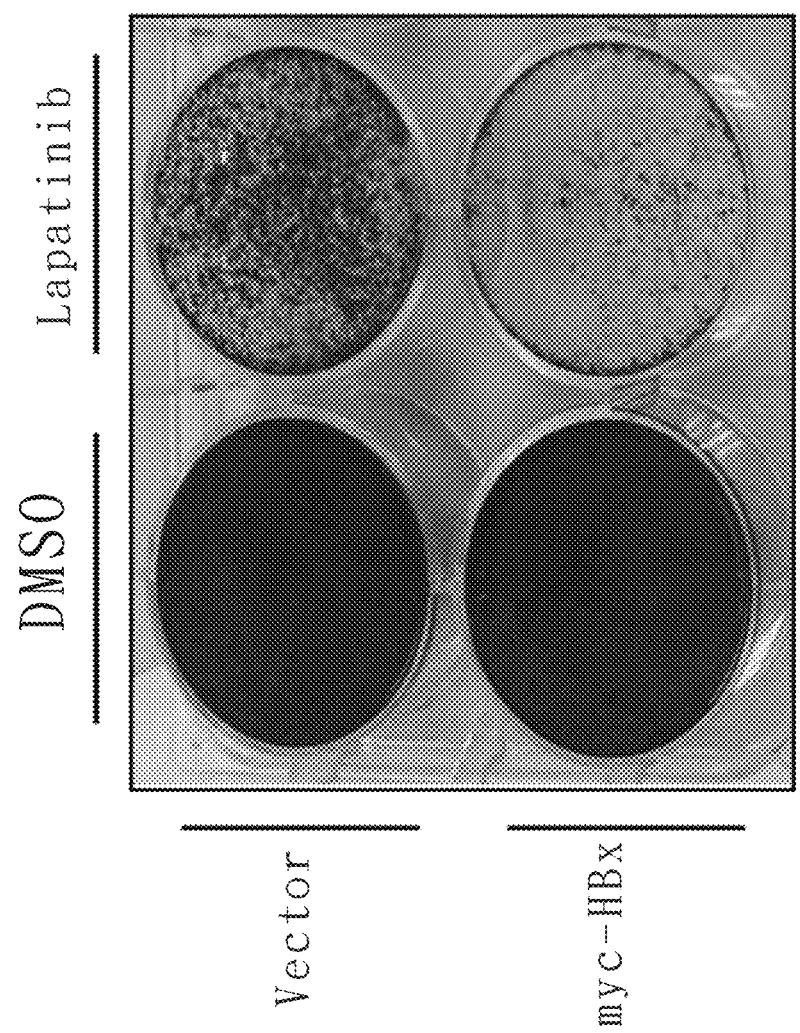
FIG. 4c shows crystal violet staining of the vector- and myc-HBx transfected Hep3B cells after lapatinib treatment.

Referring to FIG. 4c, DMSO treatment shows no difference between the vector-transfected Hep3B cells (group D1) and the myc-HBx-transfected Hep3B cells (group D2). Lapatinib treatment shows slight cytotoxicity to the vector-transfected Hep3B cells (group D1) but significant cytotoxicity to the myc-HBx-transfected Hep3B cells (group D2).

Trial (E). Lapatinib shows cytotoxicity to the HBx-virus transduced Hep3B cells.

The plasmids used to virus transduce into the Hep3B cells in the trial (E) are shown in TABLE 2. That is, pDEST-V5 vector is used as a control (group E1) and the HBx plasmid expressing HBx expression protein constructed with primers with sequences set forth in SEQ ID NOs. 7 and 8 is used as the group E2.

TABLE 2

| Groups | Plasmids |
| --- | --- |
| E1 | Vector (pDEST-V5) |
| E2 | HBx |

The plasmids are virus transduced into the Hep3B cells as the following procedure: the Hep3B cells are inoculated in 3.5-cm petri dishes with concentration of $2 \times 10^5$ cells per petri dish. After incubating for 24 hours, virus with 100 MOI is used to transduce the plasmids into the cultured Hep3B cells. Fresh media are replaced after 16 hours and the following experiments are performed 4 days later.

Figure 5A:
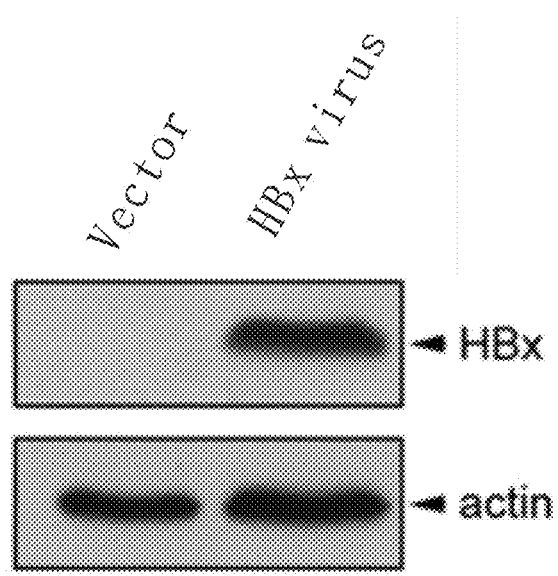
FIG. 5a shows protein level of HBx in the vector- and HBx-virus transduced Hep3B cells.

Referring to FIG. 5a, to confirm the expression of HBx, Western blotting is performed. As a result, HBx protein only expresses in the HBx-virus transduced Hep3B cells (group E2) but not the vector-virus transduced Hep3B cells (group E1).

Figure 5B:
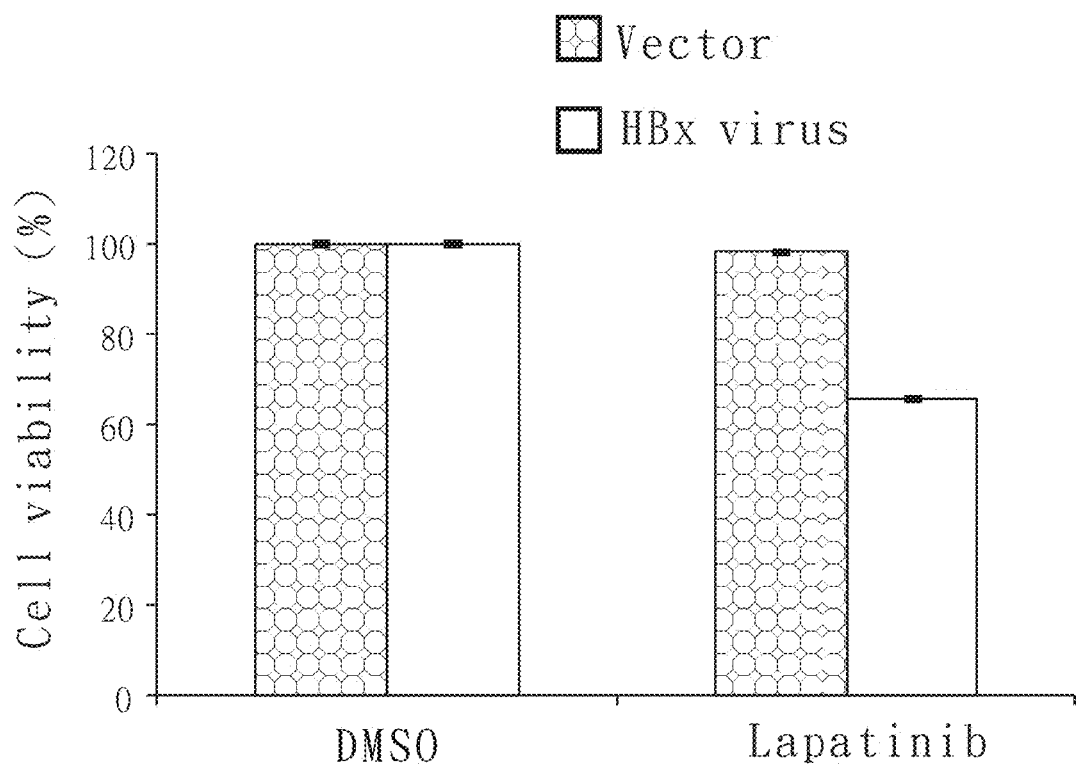
FIG. 5b shows cell viability of the vector- and HBx-virus transduced Hep3B cells after lapatinib treatment.

Furthermore, referring to FIG. 5b, DMSO treatment shows no difference between the vector-virus transduced Hep3B cells (group E1) and the HBx-virus transduced Hep3B cells (group E2). Lapatinib treatment shows no cytotoxicity to the vector-virus transduced Hep3B cells (group E1) but significant cytotoxicity to the HBx-virus transduced Hep3B cells (group E2, only about 60% cells are survival).

Accordingly, either by transient transfection or by virus transduction, the Hep3B cells can successfully express HBx, and further trigger the HBx-expressing Hep3B cells to undergo the apoptotic signaling pathway, thereby being intolerant of lapatinib.

Trial (F). Lapatinib shows cytotoxicity to the wild-type HBV genome-transfected Hep3B and HepG2 cells.

The genome of HBV contains 4 known genes including genes C, X, P and S. To define the role of HBx in cytotoxicity of lapatinib to liver cancer, the plasmids being thankful presents from Dr. Seishi Murakami (J. Virology, 79 (9): 5548-5556, 2005) are used to transiently transfect into the Hep3B cells in the trial (F). As shown in TABLE 3, the plasmid containing the wild-type HBV genome and expressing HBV pregenomic 3.5-kb RNA under the control of the endogenous promoters of HBV is used as the group F2. The plasmid containing an ochre termination signal (CAA to UAA) after codon 7 (at codon 8) in the HBx ORF is used as the group F3. The plasmids are transiently transfected into the Hep3B and HepG2 cells as described above.

TABLE 3

| Groups | Plasmids |
| --- | --- |
| F1 | Vector |
| F2 | Wild-type HBV genome |
| F3 | HBx-minus mutant |

Figure 6A:
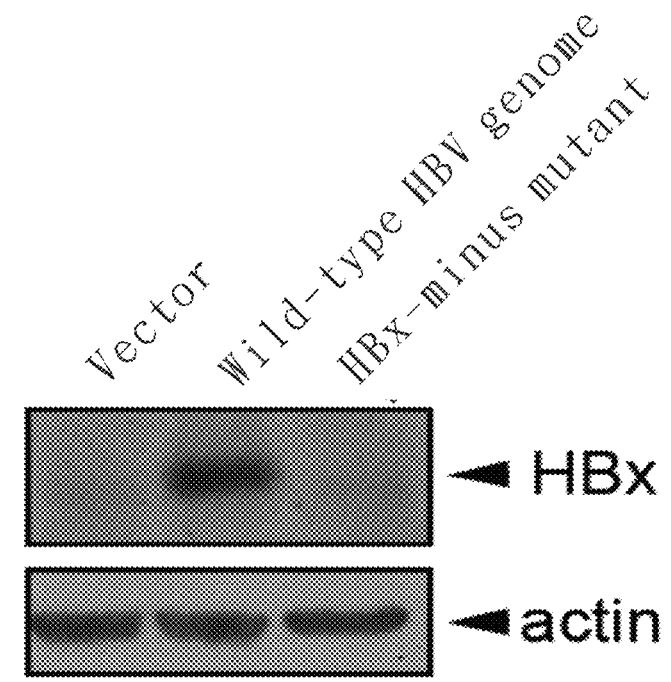
FIG. 6a shows protein level of HBx in the vector-, wild-type HBV genome- and HBx-minus mutant-transfected Hep3B cells.
Figure 6B:
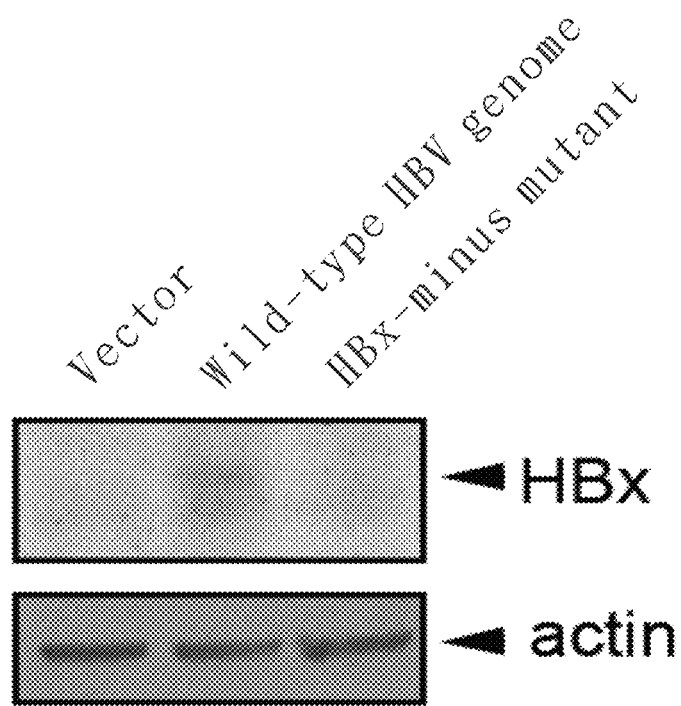
FIG. 6b shows protein level of HBx in the vector-, wild-type HBV genome- and HBx-minus mutant-transfected HepG2 cells.

Referring to FIG. 6a, HBx protein expresses in the wild-type HBV genome-transfected Hep3B cells (group F2), but not the vector- or HBx-minus mutant-transfected Hep3B cells (group F1 or F3). As shown in FIG. 6b, similar results are shown in the transfected HepG2 cells. Moreover, compared to the wild-type HBV genome-transfected Hep3B cells, the wild-type HBV genome-transfected HepG2 cells has a relative rare level of HBx protein.

Figure 6C:
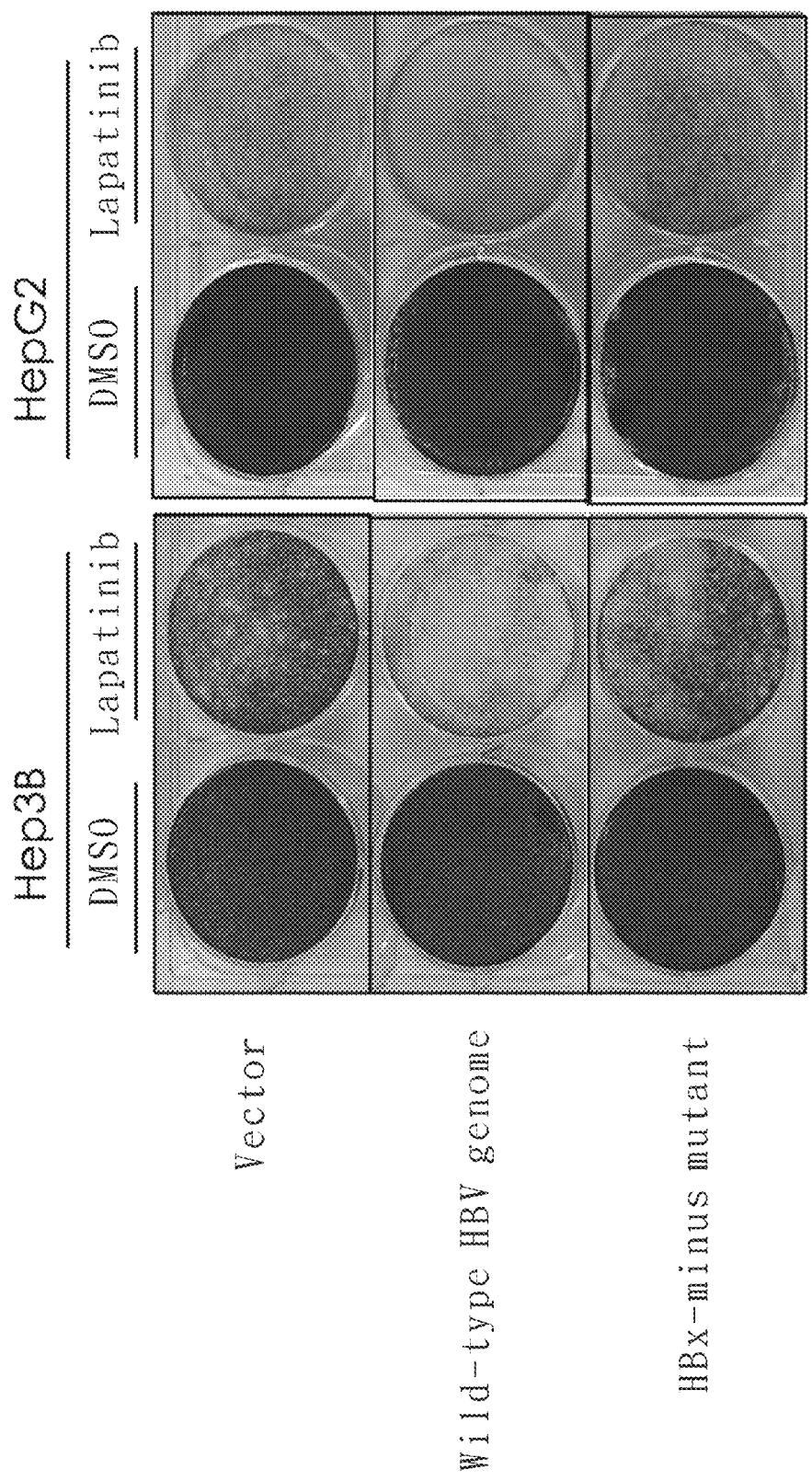
FIG. 6c shows cell viability of the vector-, wild-type HBV genome- and HBx-minus mutant-transfected Hep3B and HepG2 cells after lapatinib treatment.

The transfected Hep3B and HepG2 cells are treated with DMSO or 1 µM of lapatinib for 120 hours and the DMSO- or lapatinib-treated cells are analyzed by crystal violet assay. Referring to FIG. 6c, lapatinib shows no cytotoxicity to the vector- or HBx-minus mutant-transfected Hep3B cells (group F1 or F3), but shows obvious cytotoxicity to the wild-type HBV genome-transfected Hep3B cells (group F2). Moreover, lapatinib shows slight cytotoxicity to the vector- or HBx-minus mutant-transfected HepG2 cells (group F1 or F3). That is, the HepG2 cells are more intolerant of lapatinib in comparison of the Hep3B cells. However, comparing to the vector- or HBx-minus mutant-transfected HepG2 cells (group F1 or F3), lapatinib shows significant cytotoxicity to the wild-type HBV genome-transfected HepG2 cells with the relative rare level of HBx protein (group F2).

Accordingly, HBx protein is an indicative biomarker of whether lapatinib shows cytotoxicity to the liver cancer. Moreover, even the liver cancer with only a slight level of HBx protein is intolerant of lapatinib.

In breast cancer, lapatinib is known as a small molecular inhibitor of epidermal growth factor receptor (EGFR) family members containing EGFR, ErbB2, ErbB3 and ErbB4. However, it is still unclear whether EGFR family members are also involved in lapatinib-induced apoptosis in liver cancer.

Trial (G). Introduction of HBx increases protein level of ErbB2 and ErbB3 in the Hep3B and HepG2 cells.

To confirm the level and activity of EGFR family members in the Hep3B, Hep3Bx, HepG2 and HepG2x cells, Western blotting is performed with anti-EGFR antibody (1: 1,000, purchased from Santa Cruz), anti-pEGFR antibody (1: 1,000, specific to Tyrosine 1086 phosphorylation, purchased from Cell Signaling), anti-ErbB2 antibody (1: 1,000, purchased from Santa Cruz), anti-pErbB2 antibody (1: 1,000, specific to Tyrosine 1222, 1221 phosphorylation, purchased from Cell Signaling), anti-ErbB3 antibody (1: 1,000, purchased from Santa Cruz), anti-pErbB3 antibody (1: 1,000, specific to Tyrosine 1289 phosphorylation, purchased from Cell Signaling), anti-ErbB4 antibody (1: 1,000, purchased from Santa Cruz) and anti-pErbB4 antibody (1: 1,000, purchased from Cell Signaling). The anti-Actin antibody is used as an internal control.

Figure 7:
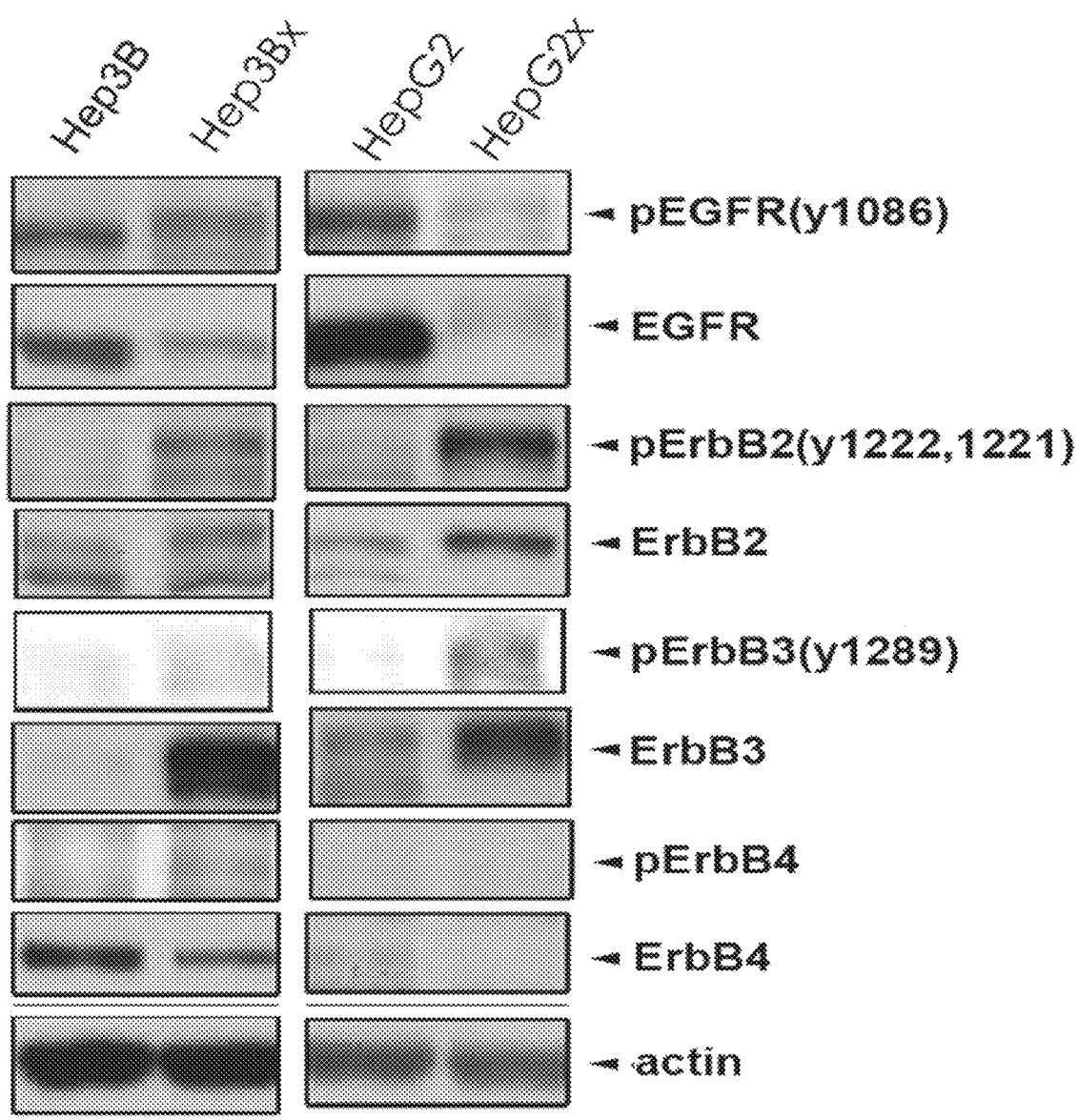
FIG. 7 shows protein level of EGFR, pEGFR, ErbB2, pErbB2, ErbB3, pErbB3, ErbB4 and pErbB4 in the Hep3B, Hep3Bx, HepG2 and HepG2x cells.

Referring to FIG. 7, compared to the Hep3B and HepG2 cells, the Hep3Bx and HepG2x cells with HBx protein show higher level of ErbB2, pErbB2, ErbB3 and pErbB3. Moreover, not only the level of ErbB2 and ErbB3 protein increases, but also the activity of ErbB2 and ErbB3 protein increases, as the level of pErbB2 and pErbB3 shown in FIG. 7. That is, introduction of HBx protein increases level and activity of ErbB2 and ErbB3.

Trial (H). Introduction of HBx increases mRNA level of ErbB3 in the Hep3B cells.

Total RNA extracted from the Hep3B or Hep3Bx cells is mixed with 50 µM, 1 µL of oligo (dT) 18 primer, and DEPC-water in a total volume of 12 µL. After incubating at 65° C. for 5 minutes, the mixture is stood on ice and further mixed with 4 µL of 5× reaction buffer, 20 units of RNase inhibitor, 2 µL of 10 mM dNTP mixture, 200 units of RevertAid™ H Minus M-MuLV in a total volume of 20 µL. The reverse transcription reaction is performed at 45° C. for 60 minutes and followed by terminating at 70° C. for 5 minutes. The final product of the reverse transcription is mixed with 1 µL of 10 µM primers for EGFR family members or actin as an internal control, respectively. The real-time PCR reaction is performed at 95° C. for 10 minutes, followed by a 45 to 60 repeating PCR cycle of 95° C. for 15 seconds and 60° C. for 1 minute.

Figure 8:
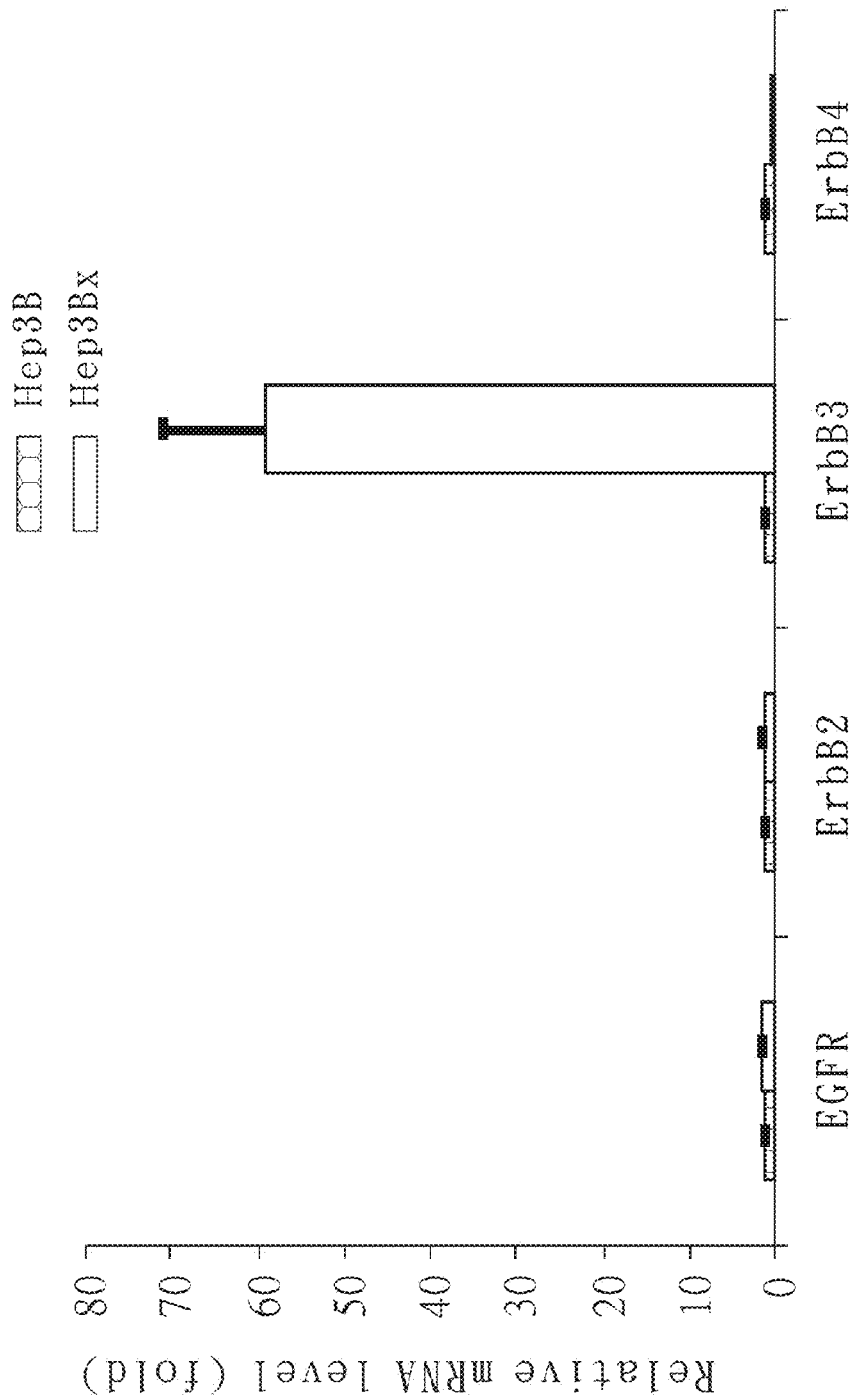
FIG. 8 shows relative mRNA level of EGFR, ErbB2, ErbB3 and ErbB4 in the Hep3B and Hep3Bx cells.

Referring to FIG. 8, the relative mRNA level of EGFR family members is calculated by dividing by mRNA level of actin. As a result, ErbB3 mRNA also increases due to the introduction of HBx in the Hep3B cells. That is, the increasing protein level of ErbB3 is as a result of the increasing mRNA level of ErbB3.

Trial (I). A positive correlation exists between level of HBx and level of ErbB3 in the Hep3B and HepG2 cells.

ErbB3, one of EGFR family member, has a genomic sequence as set forth in SEQ ID NO: 3 and an amino acid sequence as set forth in SEQ ID NO: 4.

Figure 9A:
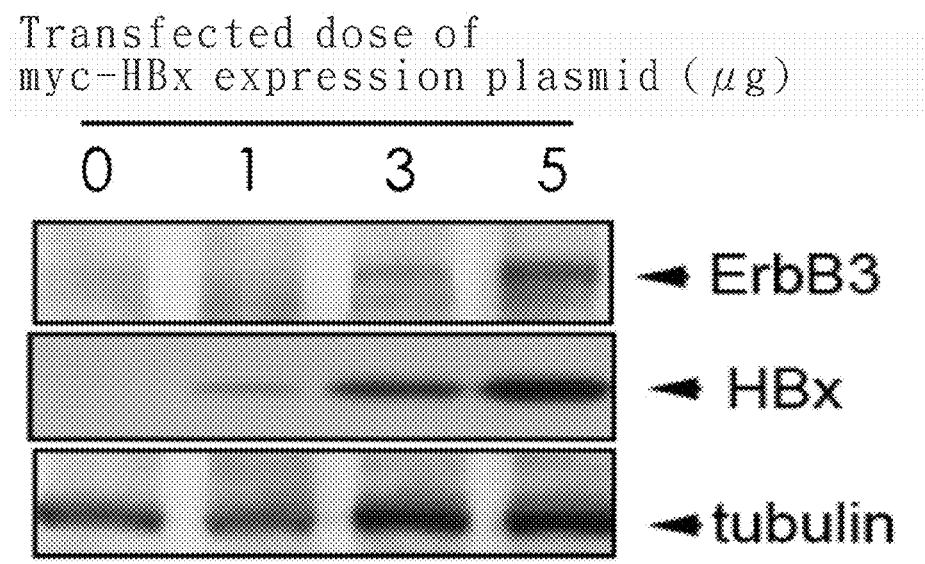
FIG. 9a shows protein level of ErbB3 and HBx in the myc-HBx-transfected Hep3B cells.

The myc-HBx expression plasmid shown in TABLE 1 is transiently transfected into the Hep3B cells in different doses (0, 1, 3 and 5 µg) and protein level of myc-HBx and ErbB3 is shown in FIG. 9a. Protein level of Tubulin is used as an internal control. That is, the higher the protein level of myc-HBx is, the higher the protein level of ErbB3 is.

Figure 9B:
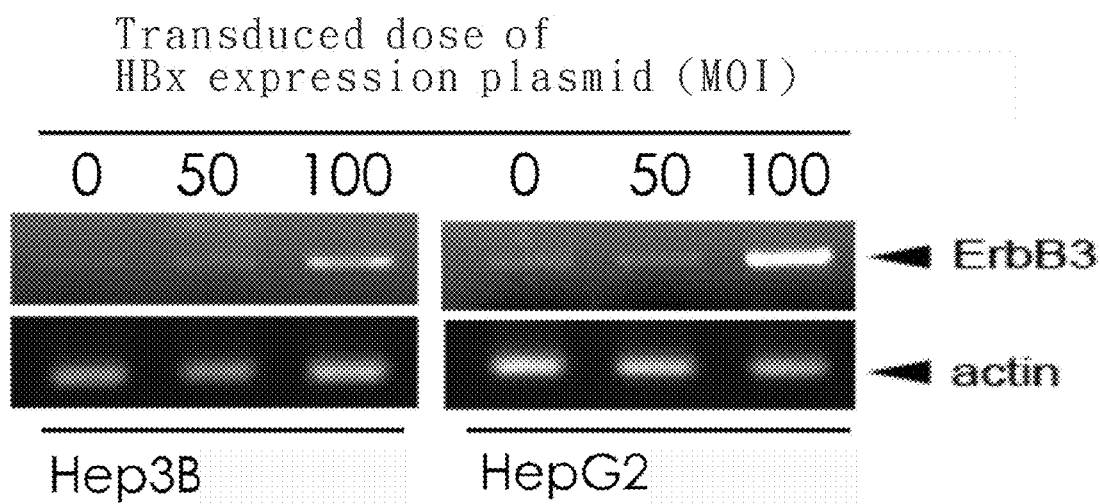
FIG. 9b shows mRNA level of ErbB3 in the HBx-virus transduced Hep3B and HepG2 cells.
Figure 9C:
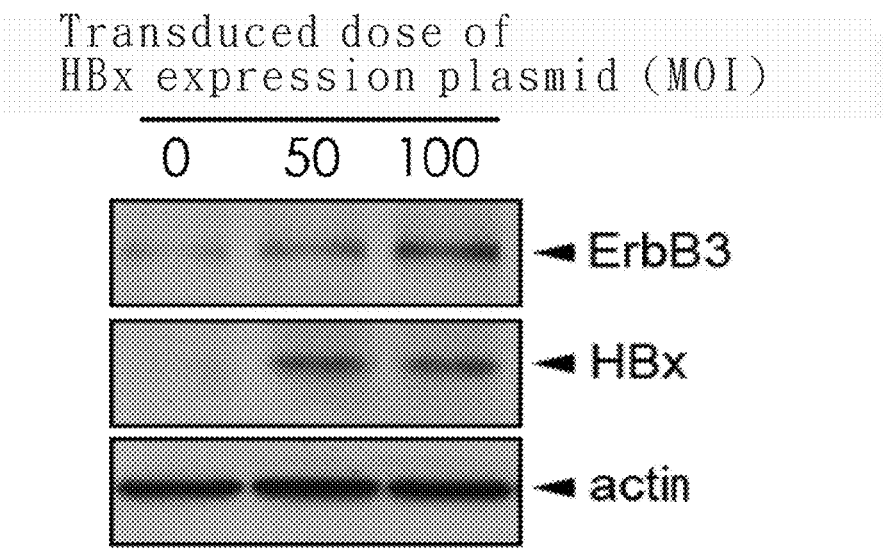
FIG. 9c shows protein level of HBx and ErbB3 in the HBx-virus transduced Hep3B cells.

The HBx expression plasmid shown in TABLE 2 is virus transduced into the Hep3B and HepG2 cells in different doses (MOI 0, 50 and 100) and mRNA level of ErbB3 detected by RT-PCR is shown in FIG. 9b. mRNA level of actin is used as an internal control. Moreover, protein level of HBx and ErbB3 is shown in FIG. 9c with actin used as an internal control. As a result, the more the HBx expression plasmid is transduced, the higher the protein level of HBx is and the higher the protein and mRNA level of ErbB3 is.

Figure 9D:
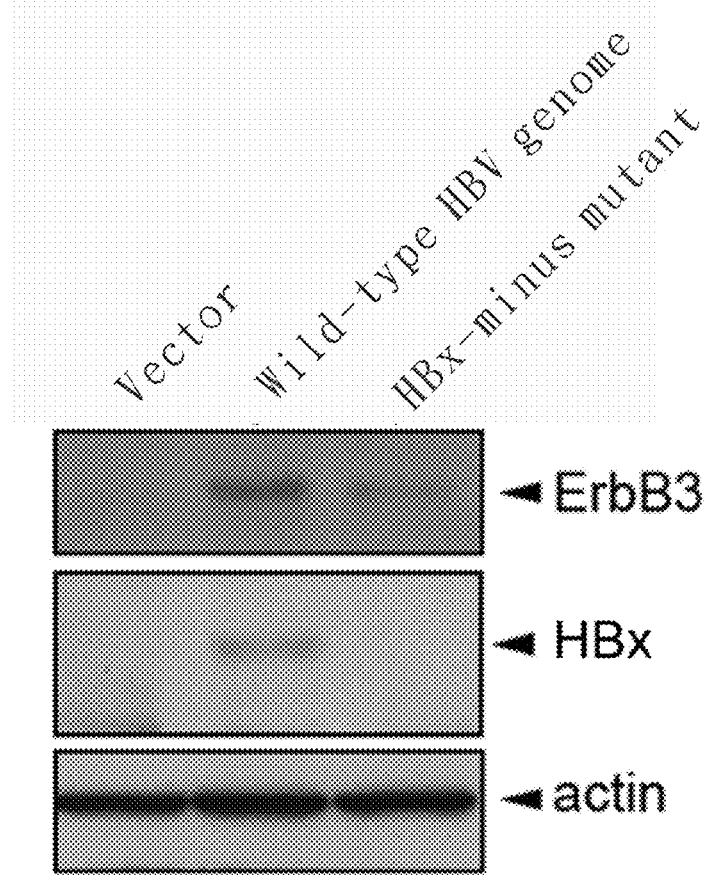
FIG. 9d shows protein level of HBx and ErbB3 in the vector-, wild-type HBV genome- and HBx-minus mutant-transfected Hep3B cells.

The vector, the wild-type HBV genome containing plasmid, and the HBx-minus mutant-containing plasmid shown in TABLE 3 are transiently transfected into the Hep3B cells. Protein level of HBx and ErbB3 are shown in FIG. 9d. As a result, both HBx and ErbB3 express in the wild-type HBV genome-transfected Hep3B cells. In the vector- or HBx-minus mutant-transfected Hep3B cells, neither HBx nor ErbB3 expresses.

HBx-specific siRNA with a sequence as set forth in SEQ ID NO: 9 and a control siRNA with a sequence as set forth in SEQ ID NO: 10 are used to further confirm the relationship between HBx and ErbB3 in the Hep3Bx cells.

5 µL of 20 µM siRNA is mixed with 1 µL of the transfection reagent and 100 µL of the medium without FBS. 30 minutes later, the siRNA-containing mixture is added into the medium-discarded Hep3Bx cells with a final volume of 1 mL. After incubating for 5 hours, the FBS containing medium as added to a final volume of 2 mL. The following experiment is performed 4-day posttransfection.

Figure 9E:
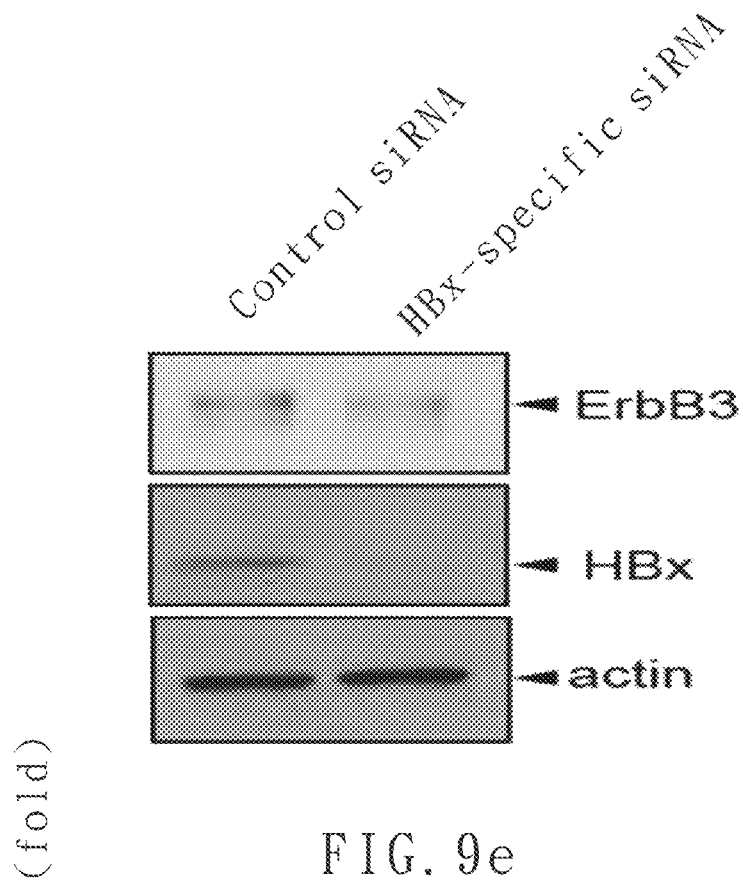
FIG. 9e shows protein level of HBx and ErbB3 in the control siRNA- and HBx-specific siRNA-treated Hep3Bx cells.

Referring to FIG. 9e, HBx-specific siRNA treatment decreases protein level of HBx, accompanying decreased protein level of ErbB3.

Accordingly, a positive correlation exists between level of HBx and level of ErbB3 in the liver cancer. Expression of HBx is capable of increasing mRNA and protein level of ErbB3.

Trial (J). mRNA level of ErbB3 increases in the HBV-associated liver cancer biopsies.

Liver cancer biopsies are obtained from liver cancer patients and grouped into a HBV-associated one (group J1) and a non-HBV-associated one (group J2). Total RNA is extracted from the liver cancer biopsies of groups J1 and J2, respectively, followed by converting to cDNA by reverse transcriptase, and lastly by detecting cDNA level of ErbB3 by performing real-time PCR.

Figure 10:
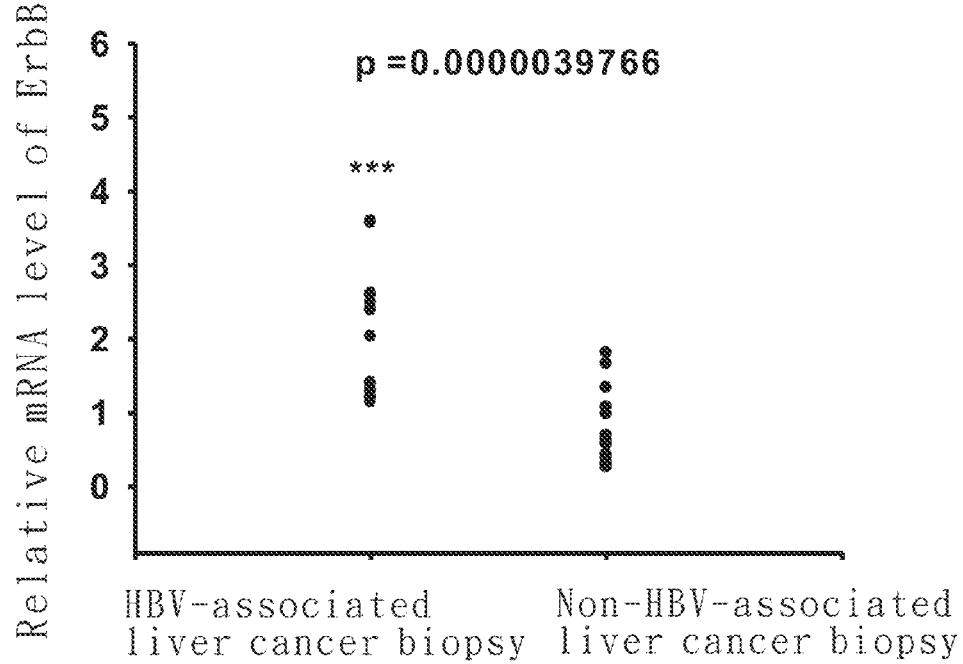
FIG. 10 shows relative mRNA level of ErbB3 in the HBV-associated and non-HBV-associated liver cancer biopsies.

Referring to FIG. 10, compared to the non-HBV-associated liver cancer biopsies (group J2), mRNA level of ErbB3 is higher in the HBV-associated liver cancer biopsies (group J1) (p=0.0000039766). That is, HBV infection-induced HBx expression can increase mRNA level of ErbB3 clinically.

Trial (K). Lapatinib shows cytotoxicity to the ErbB3-transfected Hep3B cells.

The plasmids used to transiently transfect into the Hep3B cells in the trial (K) are shown in TABLE 4. That is, pDSRed vector is used as a control (group K1) and the ErbB3 protein-expressing plasmid constructed with primers with sequences set forth in SEQ ID NOs. 11 and 12 is used as the group K2.

TABLE 4

| Groups | Plasmids |
| --- | --- |
| K1 | Vector (pDSRed) |
| K2 | ErbB3 |

Figure 11A:
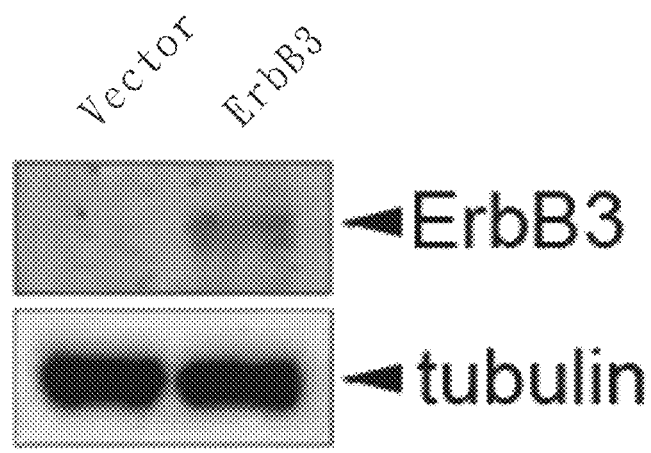
FIG. 11a shows protein level of ErbB3 in the vector- and ErbB3-transfected Hep3B cells.

Western blotting is performed to confirm the expression of ErbB3 in the vector- and ErbB3-transfected Hep3B cells. Referring to FIG. 11a, ErbB3 protein only expresses in the ErbB3-transfected Hep3B cells (group K2) but not in the vector-transfected Hep3B cells (group K1).

Figure 11B:
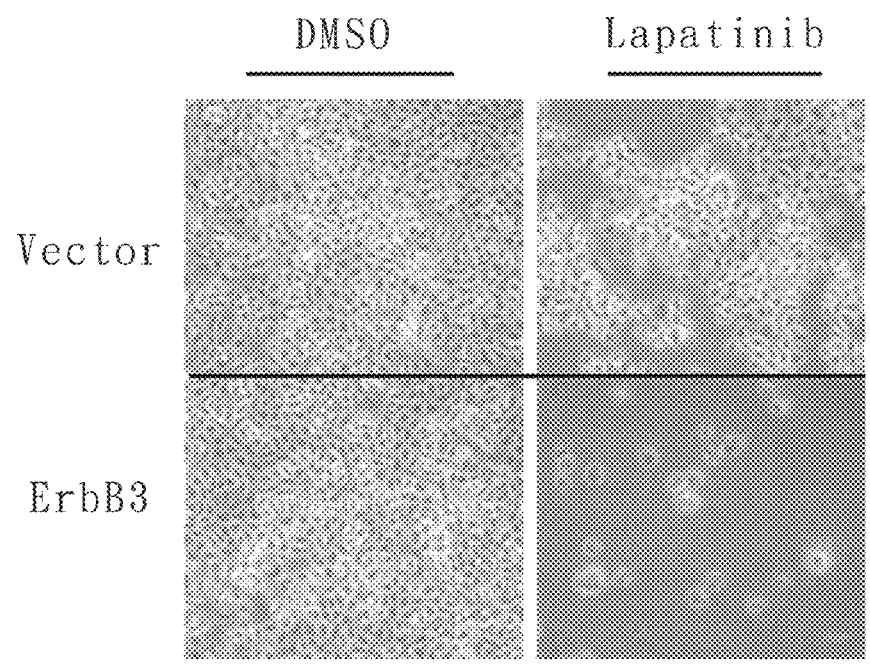
FIG. 11b shows cell numbers of the vector- and ErbB3-transfected Hep3B cells after lapatinib treatment using a light microscopy.

Referring to FIG. 11b, DMSO treatment for 120 hours shows no cytotoxicity to the vector- or ErbB3-transfected Hep3B cells. Moreover, in comparison to the vector-transfected Hep3B cells (group K1), lapatinib treatment for 120 hours triggers reduction of cell numbers of the ErbB3-transfected Hep3B cells (group K2). That is, lapatitib shows cytotoxicity to the ErbB3-transfeced Hep3B cells.

Figure 11C:
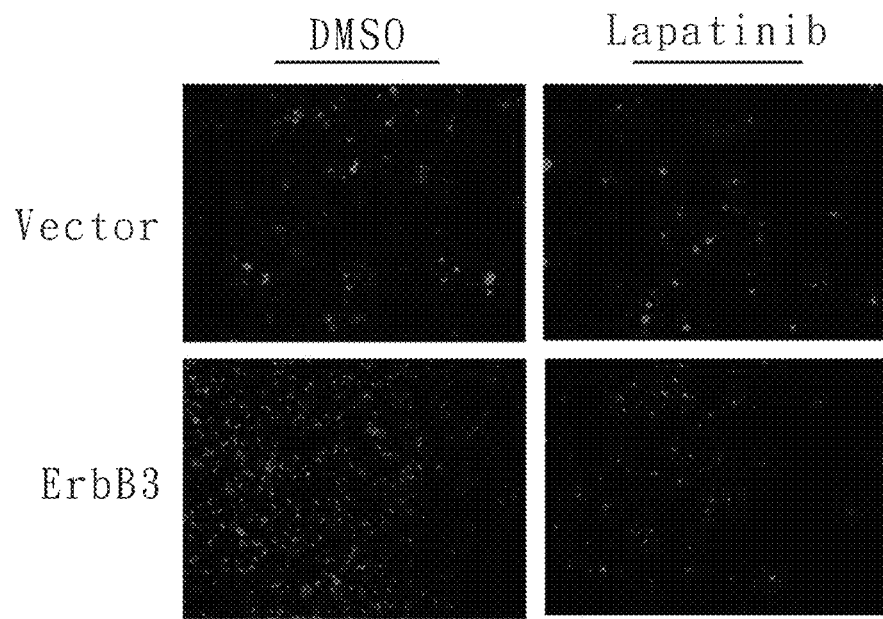
FIG. 11c shows cell numbers of the vector- and ErbB3-transfected Hep3B cells after lapatinib treatment using a fluorescence microscope.
Figure 11D:
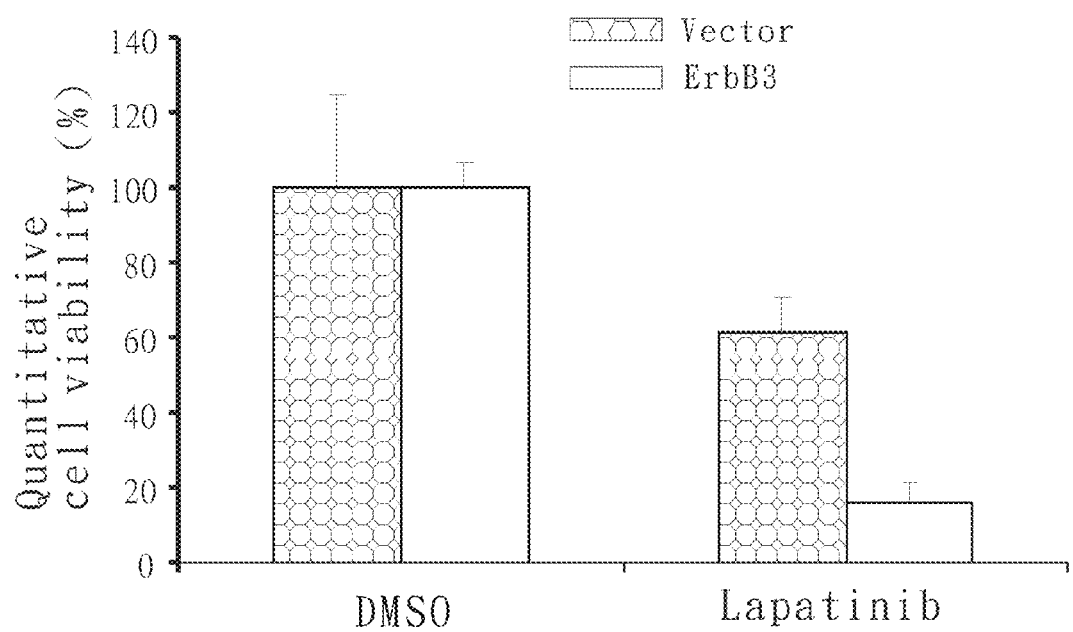
FIG. 11d shows quantitative cell viability according FIG. 11c.

Cell numbers of the vector- or ErbB3-transfected Hep3B cells are monitored using a fluorescence microscope with an excitation wavelength of 535 nm. As shown in FIG. 11c, a similar result with FIG. 11b is observed. Moreover, FIG. 11d shows a quantitative data of FIG. 11c. The cell number of the lapatinib-treated vector-transfected Hep3B cells divides by the cell number of the DMSO-treated vector-transfected Hep3B cells and the cell number of the lapatinib-treated ErbB3-transfected Hep3B cells divides by the cell number of the DMSO-treated ErbB3-transfected Hep3B cells. As a result, after lapatinib treatment for 120 hours, the quantitative cell viability of ErbB3-transfected Hep3B cells is merely smaller than 20%. That is, ErbB3 transfection induces intolerance of Hep3B cells to lapatinib.

Trial (L). ErbB3 silencing increases intolerance of the Hep3Bx cells to lapatinib.

ErbB3-specific siRNA with a sequence as set forth in SEQ ID NO: 13 is used to silence expression of ErbB3 in the Hep3Bx cells. The control siRNA with a sequence as set forth in SEQ ID NO: 10 is used as a control.

Figure 12A:
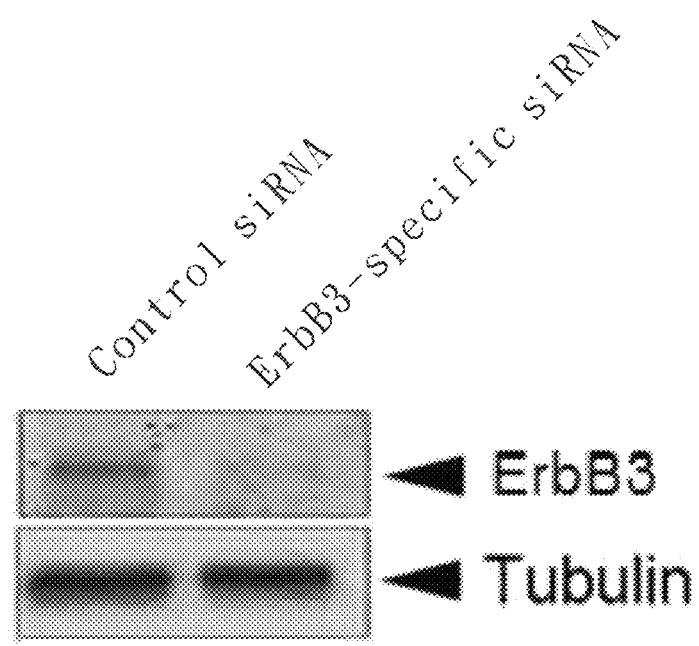
FIG. 12a shows protein level of ErbB3 in the control siRNA- and ErbB3-specific siRNA-treated Hep3Bx cells.

Referring to FIG. 12a, ErbB3-specific siRNA treatment decreases mRNA level of ErbB3, accompanying decreased protein level of ErbB3.

Figure 12B:
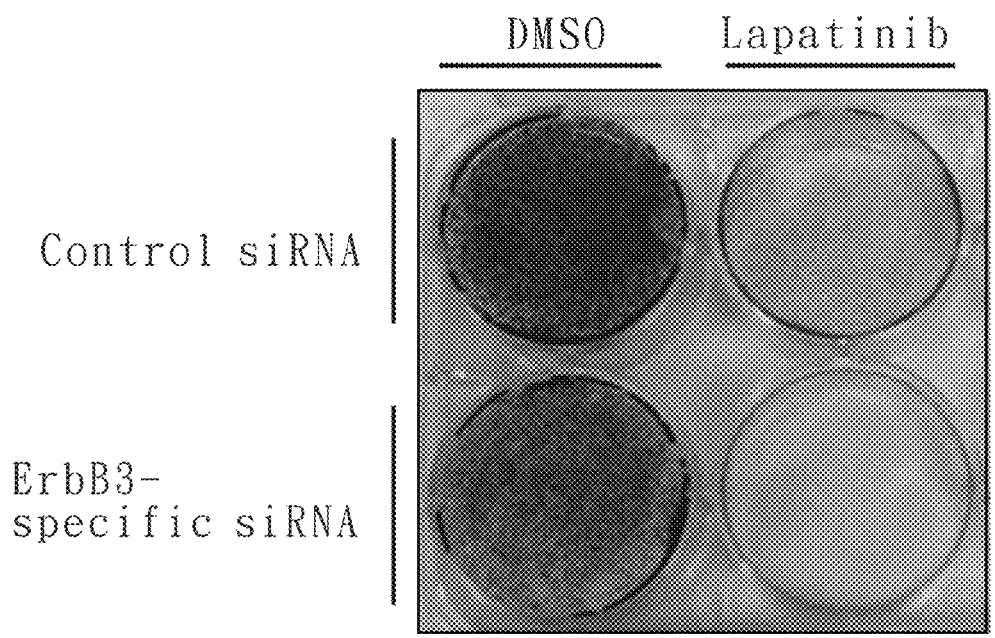
FIG. 12b shows crystal violet staining of the control siRNA- and ErbB3-specific siRNA-treated Hep3Bx cells after lapatinib treatment.

Referring to FIG. 12b, after lapatinib treatment for 120 hours, compared to the control siRNA-treated Hep3Bx cells, the ErbB3-specific siRNA-treated Hep3Bx cells are intolerance to lapatinib.

In conclusion, by comparison to the reference level of HBx or ErbB3 ex vivo, the determined level of HBx or ErbB3 from a patient's liver cancer biopsy can be used as the biomaker for evaluating therapeutic effects of lapatinib on liver cancer. According to the method for evaluating therapeutic effects of lapatinib on liver cancer according to preferred teachings of the invention, physicians are able to group the liver cancer patients into who suitable and unsuitable for lapatinib treatment, and further apply lapatinib as an anti-liver cancer drug to the former patients and thereby improving the therapeutic effects of lapatinib on liver cancer.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating liver cancer comprising:
obtaining a liver cancer biopsy from a patient;
determining level of a biomarker in the liver cancer biopsy obtained from the patient ex vivo;
comparing the determined level of the biomarker in the liver cancer biopsy obtained from the patient to a reference level of the biomarker, wherein the reference level of the biomarker is a level of the biomarker in a liver biopsy obtained from a normal, non-cancerous subject; and
administering an effective amount of lapatinib to the patient with a higher determined level of the biomarker in the liver cancer biopsy than the reference level of the biomarker;
wherein the biomarker is HBx.

2. The method for treating liver cancer as claimed in claim 1, wherein the level of the biomarker is determined by real-time PCR.

* * * * *